US012167996B2

(12) United States Patent
Evans et al.

(10) Patent No.: US 12,167,996 B2
(45) Date of Patent: Dec. 17, 2024

(54) ANTI-VIRAL COMPOSITION

(71) Applicant: Byotrol PLC, Manchester (GB)

(72) Inventors: Huw Evans, Chester (GB); Christopher Plummer, Chester (GB); Matias Luck, Wirral (GB); Rose Elizabeth Piercy McInerney, Chester (GB); Lauren Mairead Burns, Chester (GB)

(73) Assignee: BYOTROL LIMITED, Manchester (GB)

( * ) Notice: Subject to any disclaimer, the term of this patent is extended or adjusted under 35 U.S.C. 154(b) by 518 days.

(21) Appl. No.: 17/311,031

(22) PCT Filed: Dec. 5, 2019

(86) PCT No.: PCT/GB2019/053439
§ 371 (c)(1),
(2) Date: Jun. 4, 2021

(87) PCT Pub. No.: WO2020/115489
PCT Pub. Date: Jun. 11, 2020

(65) Prior Publication Data
US 2022/0023254 A1    Jan. 27, 2022

(30) Foreign Application Priority Data
Dec. 5, 2018 (GB) .................................. 1819849

(51) Int. Cl.
| | |
|---|---|
| A61K 31/357 | (2006.01) |
| A01N 31/16 | (2006.01) |
| A01N 43/32 | (2006.01) |
| A01N 65/03 | (2009.01) |
| A01P 1/00 | (2006.01) |
| A61K 31/05 | (2006.01) |
| A61K 31/085 | (2006.01) |
| A61K 36/03 | (2006.01) |
| A61P 31/12 | (2006.01) |

(52) U.S. Cl.
CPC ............ *A61K 31/357* (2013.01); *A01N 31/16* (2013.01); *A01N 43/32* (2013.01); *A01N 65/03* (2013.01); *A01P 1/00* (2021.08); *A61K 31/05* (2013.01); *A61K 31/085* (2013.01); *A61K 36/03* (2013.01); *A61P 31/12* (2018.01); *A61K 2236/333* (2013.01); *A61K 2236/55* (2013.01)

(58) Field of Classification Search
CPC .................................................... A61K 31/357
USPC ....................................................... 514/452
See application file for complete search history.

(56) References Cited

U.S. PATENT DOCUMENTS

| | | |
|---|---|---|
| 5,321,133 A | 6/1994 | Colliec et al. |
| 5,646,130 A | 7/1997 | Shi |
| 7,611,716 B2 | 11/2009 | Michailovna et al. |
| 8,101,203 B2 | 1/2012 | Cao |
| 8,748,595 B2 | 6/2014 | Shaklee et al. |
| 9,789,142 B2 | 10/2017 | Remmereit |
| 2004/0241185 A1 | 12/2004 | Chatterji et al. |
| 2007/0065526 A1 | 3/2007 | Gow et al. |
| 2007/0071839 A1 | 3/2007 | Bombardelli |
| 2007/0166415 A1 | 7/2007 | Liu |
| 2007/0218076 A1 | 9/2007 | Michailovna et al. |
| 2008/0021200 A1 | 1/2008 | Ray et al. |
| 2008/0248160 A1 | 10/2008 | Steer et al. |
| 2009/0010998 A1 | 1/2009 | Marchitto et al. |
| 2009/0042985 A1 | 2/2009 | Bhaggan |
| 2009/0155391 A1 | 6/2009 | Bhaskaran et al. |
| 2011/0171293 A1 | 7/2011 | Cao |
| 2011/0171298 A1 | 7/2011 | Cao |
| 2011/0189221 A1 | 8/2011 | van Olphen et al. |
| 2013/0225462 A1 | 8/2013 | Di Biase et al. |
| 2013/0338217 A1 | 12/2013 | Kim et al. |
| 2015/0011647 A1 | 1/2015 | Ebright et al. |
| 2017/0000817 A1 | 1/2017 | Alevizopoulos |
| 2017/0119772 A1 | 5/2017 | Lee et al. |

FOREIGN PATENT DOCUMENTS

| | | |
|---|---|---|
| CN | 101784272 A | 7/2010 |
| CN | 102579508 A | 7/2012 |
| CN | 103610704 A | 3/2014 |
| CN | 104814985 A | 8/2015 |
| CN | 105377232 A | 3/2016 |
| CN | 106070339 A | 11/2016 |
| CN | 106397169 A | 2/2017 |

(Continued)

OTHER PUBLICATIONS

Gupta et al., "Bioactive potential and possible health effects of edible brown seaweeds", 2011, Trends in Food Science & Technology, 22(6), pp. 315-326. (doi: 10.1016/j.tifs.2011.03.011) (Year: 2011).*

Venkatesan et al., "Phlorotannins", 2019, Encyclopedia of Food Chemistry, vol. 3, pp. 515-527. Available online Nov. 30, 2018. (https://doi.org/10.1016/B978-0-08-100596-5.22360-3) (Year: 2019).*

Office Action issued Apr. 25, 2022 in CN Application No. 201980080520.9.

Ahmadi et al., "Antiviral Potential of Algae Polysaccharides Isolated from Marine Sources: A Review," BioMed Research International, vol. 2015, Article ID 825203, 10 pages (2015).

(Continued)

*Primary Examiner* — Raymond J Henley, III
(74) *Attorney, Agent, or Firm* — Panitch Schwarze Belisario & Nadel LLP

(57) ABSTRACT

Phlorotannins with anti-viral properties, in particular those with a molecular mass of from about 1000 g/mol to about 3000 g/mol, are described. The phlorotannins may be obtained or obtainable as an extract from seaweed, and may be used in compositions or extracts as anti-viral agents. Methods for producing the extracts and their use for treating or preventing viral infections and for reducing or controlling a virus on a surface using the phlorotannins are also described.

17 Claims, 18 Drawing Sheets

(56) References Cited

FOREIGN PATENT DOCUMENTS

| | | | |
|---|---|---|---|
| CN | 106800546 A | 6/2017 | |
| CN | 106967085 A | 7/2017 | |
| CN | 106986852 A | 7/2017 | |
| CN | 107417697 A | 12/2017 | |
| CN | 107468718 A | 12/2017 | |
| CN | 107501287 A | 12/2017 | |
| CN | 107837247 A | 3/2018 | |
| EP | 0011322 A1 | 5/1980 | |
| EP | 0497341 A2 | 8/1992 | |
| EP | 1977756 A1 | 10/2008 | |
| EP | 2178533 A1 | 4/2010 | |
| EP | 2997963 A1 | 3/2016 | |
| GB | 1329848 A | 9/1973 | |
| JP | H07187938 A | 7/1995 | |
| JP | H0827005 A | 1/1996 | |
| JP | 2002212095 A | 7/2002 | |
| JP | 2003277203 A | 10/2003 | |
| JP | 2004189648 A | 7/2004 | |
| JP | 2005247757 A | 9/2005 | |
| JP | 2007217410 A | 8/2007 | |
| JP | 6053241 B1 | 12/2016 | |
| JP | 2018035097 A | 3/2018 | |
| JP | 2018035098 A | 3/2018 | |
| KR | 20130141874 A | 12/2013 | |
| KR | 20160077636 A | 7/2016 | |
| KR | 101772335 B1 | 9/2017 | |
| KR | 20180052258 A | 5/2018 | |
| RU | 2006117772 A | 12/2007 | |
| WO | 9109595 A1 | 7/1991 | |
| WO | 2007113646 A2 | 10/2007 | |
| WO | 2007117482 A2 | 10/2007 | |
| WO | 2008067982 A2 | 6/2008 | |
| WO | 2009005814 A2 | 1/2009 | |
| WO | 2009027057 A1 | 3/2009 | |
| WO | 2011076367 A2 | 6/2011 | |
| WO | 2011100805 A1 | 8/2011 | |
| WO | 2012093787 A2 | 7/2012 | |
| WO | 14203644 A1 | 12/2014 | |
| WO | 2015082356 A1 | 6/2015 | |
| WO | 2018088777 A1 | 5/2018 | |
| WO | 2018160001 A1 | 9/2018 | |
| WO | 2019039828 A1 | 2/2019 | |
| WO | 2019147044 A1 | 8/2019 | |

OTHER PUBLICATIONS

Araya et al., "Fucoidan therapy decreases the proviral load in patients with human T-lymphotropic virus type-1-associated neurological disease," Antiviral Therapy, vol. 16, pp. 89-98 (2011).

Austin et al., "Extracts from the edible seaweed, Ascophyllum nodosum, inhibit lipase activity in vitro: contributions of phenolic and polysaccharide components," Food & Function, vol. 9, pp. 502-510 (2018).

Berri et al., "Marine-sulfated polysaccharides extract of Ulva armoricana green algae exhibits an antimicrobial activity and stimulates cytokine expression by intestinal epithelial cells," Journal of Applied Phycology, vol. 28, pp. 2999-3008 (2016).

Blanc et al., "Radical-scavenging capacity of phenol fractions in the brown seaweed Ascophyllum nodosum: An electrochemical approach," Talanta, vol. 84, pp. 513-518 (2011).

Breton et al., Distribution and radical scavenging activity of phenols in Ascophyllum nodosum (Phaeophyceae), Journal of Experimental Marine Biology and Ecology, vol. 399, pp. 167-172 (2011).

Carlucci et al., "Antiherpetic activity and mode of action of natural carrageenans of diverse structural types," Antiviral Research, vol. 43, pp. 93-102 (1999).

Chen et al., "Aqueous Extract of the Edible Gracilaria tenuistipitata Inhibits Hepatitis C Viral Replication via Cyclooxygenase-2 Suppression and Reduces Virus-Induced Inflammation," PLOS One, vol. 8, No. 2, e57704, pp. 1-8 (2013).

Chiu et al., "Prevention of human enterovirus 71 infection by kappa carrageenan," Antiviral Research, vol. 95, pp. 128-134 (2012).

Cho et al., "Dereplication by High-Performance Liquid Chromatography (HPLC) with Quadrupole-Time-of-Flight Mass Spectroscopy (qTOF-MS) and Antiviral Activities of Phlorotannins from Ecklonia cava," Marine Drugs, vol. 17, No. 149, pp. 1-18 (2019).

Choi et al., "In vitro antibacterial and anti-inflammatory properties of seaweed extracts against acne inducing bacteria, Propionibacterium acnes," J. Environ. Biol., vol. 32, pp. 313-318 (2011).

Cooper et al., "GFS, a preparation of Tasmanian Undaria pinnatifida is associated with healing and inhibition of reactivation of Herpes," BMC Complementary and Alternative Medicine, vol. 2, No. 11, pp. 1-7 (2002).

Cox et al., "An assessment of the antioxidant and antimicrobial activity of six species of edible Irish seaweeds," International Food Research Journal, vol. 17, pp. 205-220 (2010).

Crublet et al., The HIV-1 Envelope Glycoprotein gp120 Features Four Heparan Sulfate Binding Domains, Including the Co-receptor Binding Site, The Journal of Biological Chemistry, vol. 283, No. 22, p. 15193-15200 (2008).

De S.F-TISCHER et al., "Chemical structure and antiviral activity of carrageenans from Meristiella gelidium against herpes simplex and dengue virus," Carbohydrate Polymers, vol. 63, pp. 459-465 (2006).

Dos Santos Amorim et al., "Antimicrobial Effect of a Crude Sulfated Polysaccharide from the Red Seaweed Gracilaria ornata," Brazilian Archives of Biology and Technology, vol. 55, No. 2, pp. 171-181 (2012).

El Shafay et al., "Antimicrobial activity of some seaweeds species from Red sea, against multidrug resistant bacteria," Egyptian Journal of Aquatic Research, pp. 1-10 (2015).

Eom et al., "In vitro antiviral activity of dieckol and phlorofucofuroeckol-A isolated from edible brown alga Eisenia bicyclis against murine norovirus," Algae, vol. 30, No. 3, pp. 241-246 (2015).

Fazekas et al., "Lessons learned from a double-blind randomised placebo-controlled study with a iota-carrageenan nasal spray as medical device in children with acute symptoms of common cold," BMC Complementary and Alternative Medicine, vol. 12, No. 147, pp. 1-8 (2012).

Garrido et al., "Subchronic toxicity and anti-HSV-1 activity in experimental animal of dolabelladienetriol from the seaweed, *Dictyota pfaffii*," Regulatory Toxicology and Pharmacology, vol. 86, pp. 193-198 (2017).

Gheda et al., "Antiviral Profile of Brown and Red Seaweed Polysaccharides Against Hepatitis C Virus," Iranian Journal of Pharmaceutical Research, vol. 15, No. 3, pp. 483-491 (2016).

Glombitza et al., "Fucophlorethols from the Brown Alga *Caropophyllum maschalocarpum*," Phytochemistry, vol. 30, No. 10, pp. 3423-3427 (1991).

Graiff et al., "Chemical characterization and quantification of the brown algal storage compound laminarin—A new methodological approach," J. Appl. Phycol., vol. 28, pp. 533-543 (2016).

Harden et al., "Virucidal Activity of Polysaccharide Extracts from Four Algal Species against Herpes Simplex Virus," Antiviral Res., vol. 83, No. 3, pp. 282-289 (2009).

Heffernan et al., "Profiling of the Molecular Weight and Structural Isomer Abundance of Macroalgae-Derived Phlorotannins," Marine Drugs, vol. 13, pp. 509-528 (2015).

Immanuel et al., "Effect of hot water extracts of brown seaweeds *Sargassum* spp. on growth and resistance to white spot syndrome virus in shrimp *Penaeus monodon* postlarvae," Aquaculture Research, vol. 41, pp. e545-e553 (2010).

International Preliminary Report on Patentability issued Jun. 17, 2021 in International Application No. PCT/GB2019/053439.

International Search Report issued Feb. 7, 2020 in International Application No. PCT/GB2019/053439.

Jiao et al., "Properties of Polysaccharides in Several Seaweeds from Atlantic Canada and Their Potential Anti-Influenza Viral Activities," J. Ocean Univ. China (Oceanic and Coastal Sea Research), vol. 11, No. 2, pp. 205-212 (2012).

Kadam et al., "Extraction, structure and biofunctional activities of laminarin from brown algae," International Journal of Food Science and Technology, vol. 50, pp. 24-31 (2015).

(56) References Cited

OTHER PUBLICATIONS

Kavita et al., "24-Branched Delta 5 sterols from *Laurencia papillosa* red seaweed with antibacterial activity against human pathogenic bacteria," Microbiological Research, vol. 169, pp. 301-306 (2014).

Kim et al., "Antimicrobial activity of ethanol extracts of Laminaria japonica against oral microorganisms," Anaerobe, vol. 21, pp. 34-38 (2013).

Kolanjinathan et al., "Pharmacological Efficacy of Marine Seaweed *Gracilaria edulis* Extracts Against Clinical Pathogens," Global Journal of Pharmacology, vol. 8, No. 2, pp. 268-274 (2014).

Lee et al., "Antiviral Activities against HSV-1, HCMV, and HIV-1 of Rhamnan Sulfate from Monostroma latissimum," Planta Medica, vol. 65, pp. 439-441 (1999).

Li et al., Extraction and Identification of Phlorotannins from the Brown Alga, *Sargassum fusiforme* (Harvey) Setchell, Marine Drugs, vol. 15, pp. 49-62 (2017).

Li et al., "Fucoidan from Fucus vesiculosus suppresses hepatitis B virus replication by enhancing extracellular signal-regulated Kinase activation," Virology Journal, vol. 14, No. 178, pp. 1-8 (2017).

Lopes et al., "Green seaweed *Enteromorpha compressa* (Chlorophyta, Ulvaceae) derived sulphated polysaccharides Inhibit herpes simplex virus," International Journal of Biological Macromolecules, vol. 102, pp. 605-612 (2017).

Martinez et al., "Preparation and Chromatographic Analysis of Phlorotannins," Journal of Chromatographic Science, vol. 51, pp. 825-838 (2013).

Mendes et al., "Antiviral Activity of the Green Marine Alga *Ulva fasciata* on the Replication of Human Metapneumovirus," Rev. Inst. Med. Trop. S. Paulo, vol. 52, No. 1, pp. 3-10 (2010).

Novetsky et al., "In Vitro Inhibition of Human Papillomavirus Following Use of a Carrageenan-Containing Vaginal Gel," Gynecol. Oncol., vol. 143, No. 2, pp. 313-318 (2016).

Nwosu et al., "Anti-proliferative and potential anti-diabetic effects of phenolic-rich extracts from edible marine algae," Food Chemistry, vol. 126, pp. 1006-1012 (2011).

Pantidos et al., "Phenolic-rich extracts from the edible seaweed, *Ascophyllum nodosum*, inhibit alpha-amylase and alpha-glucosidase: Potential anti-hyperglycemic effects," Journal of Functional Foods, vol. 10, pp. 201-209 (2014).

Perez et al., "Antimicrobial Action of Compounds from Marine Seaweed," Marine Drugs, vol. 14, No. 52, pp. 1-38 (2016).

Ragan et al., "Widespread Distribution of Sulfated Polyphenols in Brown Algae," Phytochemistry, vol. 18, pp. 261-262 (1979).

Ravikumar et al., "In vitro antiplasmodial activity of ethanolic extracts of seaweed macroalgae against Plasmodium falciparum," Parasitol Research, vol. 108, pp. 1411-1416 (2011).

Rodriguez et al., "In vitro and in vivo evaluation of two carrageenan-based formulations to prevent HPV acquisition," Antiviral Research, vol. 108, pp. 88-93 (2014).

Spicer et al., "Novel rapid method for the characterisation of polymeric sugars from macroalgae," J. Appl. Phycol., vol. 29, pp. 1507-1513 (2017).

Steevensz et al., "Profiling Phlorotannins in Brown Macroalgae by Liquid Chromatography-High Resolution Mass Spectrometry," Phytochemical Analysis, 7 pages (2012).

Talarico et al., "The antiviral activity of sulfated polysaccharides against dengue virus is dependent on virus serotype and host cell," Antiviral Research, vol. 66, pp. 103-110 (2005).

Thompson et al., "Antiviral Activity of Undaria pinnatifida against Herpes Simplex Virus," Phytotherapy Research, vol. 18, pp. 551-555 (2004).

Tierney et al., "Enrichment of polyphenol contents and antioxidant activities of Irish brown macroalgae using food-friendly techniques based on polarity and molecular size," Food Chemistry, vol. 139, pp. 753-761 (2013).

Tierney et al., UPLC-MS profiling of low molecular weight phlorotannin polymers in Ascophyllum nodosum, Pelvetia canaliculata and Fucus spiralis, Metabolomics, vol. 10, pp. 524-535 (2014).

Wang et al., "Structural features and anti-HIV-1 activity of novel polysaccharides from red algae *Grateloupia longifolia* and *Grateloupia filicina*," International Journal of Biological Macromolecules, vol. 41, pp. 369-375 (2007).

Written Opinion issued Feb. 7, 2020 in International Application No. PCT/GB2019/053439.

Zhu et al., "Antiviral property and mode of action of a sulphated polysaccharide from Sargassum patens against herpes simplex virus type 2," International Journal of Antimicrobial Agents, vol. 24, pp. 81-85 (2004).

* cited by examiner

ANTI-VIRAL COMPOSITION

CROSS-REFERENCE TO RELATED APPLICATIONS

This application is a Section 371 of International Application No. PCT/GB2019/053439, filed Dec. 5, 2019, which was published in the English language on Jun. 11, 2020 under International Publication No. WO 2020/115489 A1, which claims priority under 35 U.S.C. § 119 (b) to British Application No. 1819849.9, filed on Dec. 5, 2018, the disclosures of which are incorporated herein by reference in their entireties.

This invention relates to phlorotannins with anti-viral properties which may be obtained or obtainable as an extract from seaweed, including the use of the phlorotannins or the extract as an anti-viral agent. In addition, the use of the phlorotannins or the extract in a composition with anti-viral properties and the use of said composition as an anti-viral agent.

The listing or discussion of an apparently prior-published document in this specification should not necessarily be taken as an acknowledgement that the document is part of the state of the art or is common general knowledge.

Seaweed or macroalgae is typically divided into 3 types, red (Rhodophyta), brown (Phaeophyta), and green (Chlorophyta). There is a fourth type of algae, the tuft-forming blue-green algae (Cyanobacteria) that is sometimes considered to be seaweed. There are about 10,000 species of seaweeds, of which, approximately, 6,500 are red algae, 2,000 are brown algae and 1,500 are green algae.

Brown algae (or brown seaweed) is the largest type of seaweed. Brown algae may be brown or yellow-brown in colour and is typically found in temperate or arctic waters in the northern hemisphere. Brown algae typically have a root-like structure called a "holdfast" to anchor the algae to a surface.

Whilst Red and brown algae are almost exclusively marine, green algae are also common in freshwater (rivers and lakes), and even in terrestrial (rocks, walls, houses, and tree bark in damp places) situations.

Polyphenolic compounds are present in a variety of terrestrial and marine plants. A class of polyphenolics known as Phlorotannins are only found in brown seaweed. Phlorotannins are formed through polymerisation of phloroglucinol units.

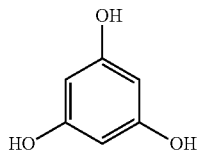

Phloroglucinol (1,3,5-trihydroxybenzene)

Phlorotannins are produced by seaweed as secondary metabolites and biosynthesized via the acetate malonate pathway. They are present in the seaweed in free form or forming complexes with different components of the cell wall, such as alginic acid. Phlorotannins are essential to the physiological integrity of seaweed and involved in several important secondary roles such as chemical defence, protection against oxidative damage that occurs in response to changes in nutrient availability and UV radiation, interactions with other organisms or the abiotic environment, as well as being integral components of cell wall.

In general, phlorotannins are separated into four sub-classes; based on the bonding type between phloroglucinol units and/or the presence of additional hydroxyl groups, the sub-classes are as follow:
1. Phlorotannins with an ether linkage (i.e. phloroethols and fuhalols, fuhalols are constructed of phloroglucinol units that are connected with para- and ortho-arranged ether bridges, containing one additional OH-group in every third ring).
2. Phlorotannins with a phenyl linkage (i.e. fucols).
3. Phlorotannins with an ether and a phenyl linkage (i.e. fucophlorethols)
4. Phlorotannins with a dibenzodioxin linkage. (i.e. eckols and carmalols)

Examples of the types of linkage in phlorotannin are illustrated below:

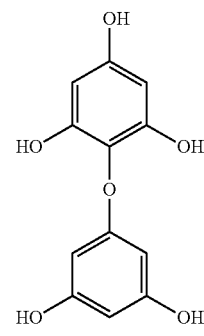

Ether linkage

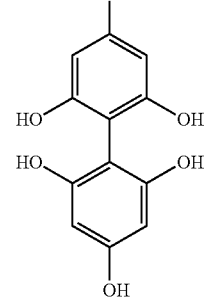

Phenyl linkage

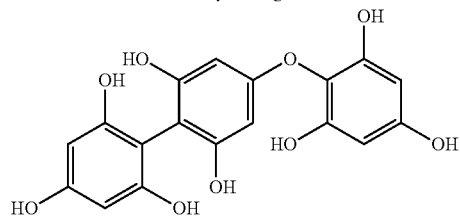

Ether and phenyl linkage

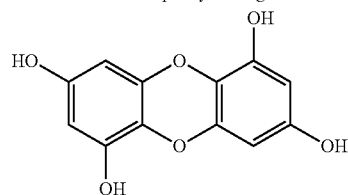

Dibenzodioxin Linkage

The molecular weight of these compounds can range from 126 to greater than $10^5$ g/mol. The amount of polyphenols in a seaweed vary with habitat, time of harvest, light intensity exposure and nutrient availability in the surrounding waters as well as the species.

The total content of phenolic compounds, including phlorotannins, is typically measured by colorimetric assays such as the Folin-Ciocalteu method and the concentration of phenolics typically range from 0.1 to 20% of the dry mass of the seaweed, again dependant on the above factors. A liquid chromatographic method combined with mass spectrometry, sometimes supplemented by high resolution NMR can be used to provide information on the chemical composition of the phenolic content.

Using these techniques it is possible to obtain information such as the degree of polymerisation (DP) of the phloroglucinol unit, the molecular mass, the bonding type between phloroglucinol units, and the isomers present. Due to the complexity and huge diversity of chemical species present such studies are far from straightforward, requiring significant effort and experimental techniques to extract and fractionate the phlorotannin and then analyse and interpret results.

It is an object of the invention to provide an anti-viral agent obtained or obtainable from a natural source.

The present inventors have surprisingly found that extracts obtained or obtainable from seaweed, such as brown seaweed, comprising polyphenols, such as phlorotannins, have anti-viral activity.

According to the present invention, there is provided a phlorotannin or a mixture of phlorotannins for use as an anti-viral agent. In particular, a phlorotannin or a mixture of phlorotannins having a molecular mass of from about 1000 g/mol to about 3000 g/mol for use as an anti-viral agent. The phlorotannins may be used to treat or prevent viral infection.

There is also provided, the use of one or more phlorotannins as an anti-viral agent, such as an agent to treat or prevent viral infection. In particular, the use of one or more phlorotannins having a molecular mass of from about 1000 g/mol to about 3000 g/mol as an anti-viral agent.

There is also provided the use of one or more phlorotannins in the manufacture of an anti-viral composition, such as a composition to be used to treat or prevent viral infection. In particular, the use of one or more phlorotannins having a molecular mass of from about 1000 g/mol to about 3000 g/mol in the manufacture of an anti-viral composition, such as a composition to be used to treat or prevent viral infection.

The phlorotannins of the present invention may be provided as an extract obtained from or obtainable from seaweed.

Thus, according to the present invention, there is provided an extract obtained from or obtainable from seaweed, which may be referred to hereinafter as the "extract of the invention".

The extracts of the invention comprise polyphenols. The phenolic compounds present in the extract of the invention typically comprise oligomers of at least 2 phloroglucinol units, known as phlorotannins. In particular, the extracts of the invention comprise one or more phlorotannins.

The extract of the invention may be obtained from or obtainable from at least one seaweed selected from brown, green and red seaweed. For example, the seaweed may be obtained or obtainable from brown seaweed.

For example, the extract of the invention may be obtained from or obtainable from at least one seaweed from the seaweed families: Fucaceae, Himanthaliaceae, Durvillaeaceae, Laminariaceae, Alariaceae and/or Sargassaceae.

In particular, the extract of the invention may be obtained from or obtainable from at least one seaweed selected from one or more of the following genera: *Ascophyllum, Fucus, Hesperophycus, Pelvetia, Pevetiopsi Silvetia, Himanthalia, Durvillaea, Anthrothamnus, Costularia, Cymathere, Feditia, Laminaria, Macrocystis, Nereocystis, Pelagophycus, Phyllariella, Postelsia, Pseudolessonia, Saccharina, Steptophyllopsis, Alaria, Aureophycus, Eualaria, Lessoniopsis, Pleurophycus, Undaria, Undariella, Undariopsis Acrocarpia, Acystis, Anthophycus, Axillariella, Bifurcaria, Carpoglossum, Carpophyllum, Caulocystis, Cladophyllum, Coccophora, Cystophora, Cystophyllum, Cystoseira, Halidrys, Hizikia, Hormophysa, Landsburgia, Myagropsis, Myriodesma, Nizamuddinia, Oerstedtia, Platythalia, Sargassum, Scaberia*, and/or *Turbinaria*.

For example, the extract of the invention may be obtained or obtainable from *Ascophyllum nodosum*.

As will be appreciated by the person skilled in the art, as used herein the term "obtainable from" means that the extract may be obtained from a seaweed or may be isolated from the seaweed, or may be obtained from an alternative source, for example by chemical synthesis or enzymatic production. Whereas the term "obtained" as used herein, means that the extract is directly derived from the seaweed source.

The extract of the present invention may comprise from about 1% to about 100% by weight, such as from about 1% to 95% by weight, or 2 to 90% by weight or 2% to about 80% or from about 5% to about 70% or from about 8% to about 65% by weight of phlorotannins based on the dry weight of the extract.

A crude extract of the present invention will typically comprise, in addition to the phlorotannins, polysaccharides such as fucoidans and laminarans, monosaccharides such as mannitol and minerals such as sodium chloride. Typically, phlorotannins will be present in a crude extract in an amount of about 1% to about 20% or about 30% of the extract. Purification techniques known in the art can be used to remove materials such as polysaccharides and monosaccharides and thereby increase the concentration of phlorotannins.

Extractions of the invention that have been subjected to one or more purification steps may comprise up to about 100% by weight of phlorotannins based on the dry weight of the extract. For example, such extracts may comprise at least about 50% by weight based on the dry weight of the extract of phlorotannins. These extracts of the invention may comprise from about 50% to about 100% by weight based on the dry weight of the extract of phlorotannins, for example from about 60 to about 95% or from about 70 to about 90% by weight based on the dry weight of the extract.

The phlorotannins of the present invention, such as those present in an extract of the invention may, for example, comprise an average of at least about 2 or at least about 10 phloroglucinol units, for example an average of from about 10 to about 50 phloroglucinol units, such as an average of from about 10 to about 30 or from about 10 to about 25 or from about 10 to about 23 phloroglucinol units.

The phlorotannins of the present invention, such as those present in an extract of the invention may comprise at least about 70% by weight based on the dry weight of the phlorotannins in the dry extract of phlorotannins having an average of at least 10 phloroglucinol units, such as an average from about 10 to 23 phloroglucinol units. For example, from about 75% to about 100% or from about 80% to about 95% by weight of such phlorotannins based on the dry weight of the phlorotannins in the dry extract.

The phlorotannins of the present invention, such as those present in an extract of the invention may comprise at least about 70% by weight based on the dry weight of the phlorotannins in the dry extract, phlorotannins having an average molecular mass over 250 g/mol. For example, from about 75% to about 100% or from about 80% to about 95% by weight of such phlorotannins based on the dry weight of the phlorotannins in the dry extract.

The phlorotannins of the present invention, such as those present in an extract of the invention may comprise at least about 70% by weight based on the dry weight of the phlorotannins in the dry extract of phlorotannins having an average molecular mass over 1000 g/mol such as from about 1000 g/mol to about 3000 g/mol, such as from about 1200 g/mol to about 2500 g/mol. For example, from about 75% to about 100% or from about 80% to about 95% by weight of such phlorotannins based on the dry weight of the phlorotannins in the dry extract having an average molecular mass over 1000 g/mol such as from about 1000 g/mol to about 3000 g/mol, such as from about 1200 g/mol to about 2500 g/mol.

The phlorotannins of the present invention, such as those present in an extract of the invention may have an average molecular mass over 1000 g/mol such as from about 1000 g/mol to about 3000 g/mol, such as from about 1200 g/mol to about 2500 g/mol.

For example, less than 20% by weight of the phlorotannins may have an average molecular mass less than 1000 g/mol or greater than 3000 g/mol, such as less than 10% or less than 5%. In some aspects, the phlorotannins of the present invention, such as those present in the extract of the invention may not have an average molecular mass less than 1000 g/mol or greater than 3000 g/mol.

The phloroglucinol units which make up the phlorotannins of the present invention, such as those present in an extract of the invention may be linked through at least one of the linkages selected from a group consisting of: phenyl linkage, ether linkage, and dibenzodioxin linkages and combinations thereof.

The phloroglucinol units which make up the phlorotannins of the present invention, such as those present in an extract of the invention may be linked to form linear chains, branched chains or a mixture thereof.

Some extracts of the present invention may comprise no polysaccharides derived from or derivable from seaweed (ie: be free of polysaccharides) or comprises a small amount of polysaccharides derived from or derivable from seaweed (ie: be substantially free of polysaccharides), for example from about 0% to about 30% or from about 0% to about 20%, such as from about 0% to about 10% or from about 0% to about 5% or from about 0% to about 1% based on the dry weight of the extract.

For example, the extract of the invention may have been purified using techniques known in the art to remove polysaccharides, such as using solid phase extract (SPE) or tangential flow filtration (TFF). Such an extract may be referred to as a purified extract of the invention.

Some extracts of the present invention may comprise no anti-viral polysaccharides derived from or derivable from seaweed (ie: be free of anti-viral polysaccharides) or comprises a small amount of anti-viral polysaccharides derived from or derivable from seaweed (ie: be substantially free of anti-viral polysaccharides), for example from about 0% to about 30% or from about 0% to about 20%, such as from about 0% to about 10% or from about 0% to about 5% or from about 0% to about 1% based on the dry weight of the extract.

Some extracts of the present invention may comprise no fucoidan derived from or derivable from seaweed (ie: be free of fucoidan) or comprises a small amount of fucoidan derived from or derivable from seaweed (ie: be substantially free of fucoidan), for example from about 0% to about 30% or from about 0% to about 20%, such as from about 0% to about 10% or from about 0% to about 5% or from about 0% to about 1% based on the dry weight of the extract.

The phlorotannins of the present invention, such as those present in an extract of the invention may be obtained via extraction and/or isolation from biological material, such as seaweed.

Solvents used for extraction and/or isolation maybe water, alcoholic, organic or mixtures thereof.

The term "aqueous extract" as used herein, refers to phlorotannins and/or an extract obtained from seaweed when the extraction from the seaweed has been performed using water as the only solvent.

The term "alcohol extract" as used herein, refers to phlorotannins and/or an extract obtained from seaweed when the extraction from the seaweed has been performed using an alcohol as the solvent. The alcohol solvent may consist of only alcohol (e.g. 100% alcohol), for example 100% ethanol.

The term "hydroalcoholic extract" as used herein, refers to phlorotannins and/or an extract obtained from seaweed when the extraction from the seaweed has been performed using a mixture of an alcohol and water as the solvent. For example, from about 1% to about 99% alcohol in water. For example, a mix of ethanol and water. For example, the solvent may be 10%, 20%, 30%, 40%, 50%, 60%, 70%, 80%, or 90% alcohol in water, such as 60% alcohol in water (based on the total amount of solvent, including water present in the seaweed, if fresh seaweed is used). For example, the solvent may be from about 10% alcohol (i.e. ethanol) in water to about 90% alcohol in water, such as from about 20% to about 80% or from about 30% to about 70% or 40% to about 60%. Alcohols that may be mentioned include ethanol (EtOH, hydro-ethanolic) and methanol (MeOH, hydro-methanolic). The use of a hydro-ethanolic extraction solvent is preferred in some aspects of the invention.

The term "organic extract" as used herein, refers to phlorotannins and/or an extract obtained from seaweed when the extraction from the plant has been performed using an organic solvent that is not an alcohol as the solvent. For example, the organic solvent, may be selected from the group consisting of acetic acid, acetone, acetonitrile, benzene, 1-butanol, 2-butanol, 2-butanone, carbon tetrachloride, chlorobenzene, chloroform, cyclohexane, 1,2-dichloroethane, diethylene, glycol, diethyl ether, diglyme (diethylene glycol, dimethyl ether), 1,2-dimethozy-ethane (glyme, DME), dimethyl formamide (DMF), dimethyl sulfoxide (DMSO), 1,4-dioxane, ethyl acetate, ethylene glycol, glycerine, heptane, hexamethylphosphoramide (HMPA), hexamethylphosphorous triamide (HMPT), hexane, methyl t-butyl, ether (MTBE), methylene chloride, N-methyl-2-pyrrolidinone (NMP), nitromethane, pentane, petroleum ether (ligroin), 1-propanol, 2-propanol, pyridine, tetrahydrofuran (THF), toluene, triethyl amine, o-xylene, m-xylene and p-xylene.

For example, the phlorotannins of the present invention and/or an extract of the invention may be obtained or obtainable from brown seaweed using a hydroalcoholic extraction solvent (i.e. be a hydroalcoholic extract).

The use of a hydroalcoholic solvent may allow for the selective extraction of lower molecular weight and/or more water-soluble compounds from the seaweed (such as brown seaweed). For example, where the extract of the invention is a hydroalcoholic brown seaweed extract (i.e. a hydroethanolic extract), the one or more phlorotannins may have from about 10 to about 30 or from about 10 to about 23 phloroglucinol units and/or an average molecular mass of 1000 g/mol or greater, such as from about 1000 g/mol to about 3000 g/mol or from about 12000 g/mol to about 2500 g/mol.

For example, the extract may be obtained or obtainable from brown seaweed comprising one or more phlorotannins, wherein at least about 70% by weight based on the dry weight of the phlorotannins in the dry extract have a molecular mass of from about 1000 g/mol to about 3000 g/mol based on the dry weight of the extract.

By the term water soluble we mean that at least about 2% (i.e. at least about 2 g per 100 ml), such as at least about 5%, 10%, 20%, 40%, 60%, or 70% (i.e. at least about 5 g, 10 g, 20 g, 40 g, 60 g, or 70 g per 100 ml) of the composition will dissolve in water at room temperature, i.e. a temperature of about 25° C.

The extract of the invention may be obtained or obtainable from brown seaweed using a hydroalcoholic (hydroethanolic) extraction solvent (i.e. a hydroalcoholic (hydroethanolic) extract), wherein the extract comprises from about 1% to about 100% by weight, such as from about 1% to 95% by weight, or 2 to 90% by weight or 2% to about 80% or from about 5% to about 70% or from about 8% to about 65% by weight of one or more phlorotannins based on the dry weight of the extract.

The extract of the invention may be obtained or obtainable from brown seaweed using a hydroalcoholic (hydroethanolic) extraction solvent (i.e. a hydroalcoholic (hydroethanolic) extract), wherein the extract comprises from about 1% to about 100% by weight, such as from about 1% to 95% by weight, or 2 to 90% by weight or 2% to about 80% or from about 5% to about 70% or from about 8% to about 65% by weight of one or more phlorotannins based on the dry weight of the extract, wherein the one or more phlorotannins have from about 10 to about 30 phloroglucinol units or from about 10 to about 23 phloroglucinol units, for example, wherein at least about 70% by weight based on the dry weight of the phlorotannins in the dry extract have from about 10 to about 30 phloroglucinol units or from about 10 to about 23 phloroglucinol units.

The extract of the invention may be obtained or obtainable from brown seaweed using a hydroalcoholic (hydroethanolic) extraction solvent (i.e. a hydroalcoholic (hydroethanolic) extract), wherein the extract comprises from about 1% to about 100% by weight, such as from about 1% to 95% by weight, or 2 to 90% by weight or 2% to about 80% or from about 5% to about 70% or from about 8% to about 65% by weight of one or more phlorotannins based on the dry weight of the extract and the one or more phlorotannins have an average molecular mass of 1000 g/mol or greater, such as from about 1000 g/mol to about 3000 g/mol or from about 1200 g/mol to about 2500 g/mol, for example, wherein at least about 70% by weight based on the dry weight of the phlorotannins in the dry extract have a molecular mass of from about 1000 g/mol to about 3000 g/mol based on the dry weight of the extract.

The extract of the invention may be obtained or obtainable from brown seaweed using a hydroalcoholic (hydroethanolic) extraction solvent (i.e. a hydroalcoholic (hydroethanolic) extract), wherein the extract comprises from about 1% to about 100% by weight, such as from about 1% to 95% by weight, or 2 to 90% by weight or 2% to about 80% or from about 5% to about 70% or from about 8% to about 65% by weight of one or more phlorotannins based on the dry weight of the extract, wherein the one or more phlorotannins have from about 10 to about 30 phloroglucinol units or from about 10 to about 23 phloroglucinol units and have an average molecular mass of 1000 g/mol or greater, such as from about 1000 g/mol to about 3000 g/mol or from about 1200 g/mol to about 2500 g/mol, for example, wherein at least about 70% by weight based on the dry weight of the phlorotannins in the dry extract have from about 10 to about 30 phloroglucinol units or from about 10 to about 23 phloroglucinol units and/or have a molecular mass of from about 1000 g/mol to about 3000 g/mol based on the dry weight of the extract.

The purified extract of the invention may be obtained or obtainable from brown seaweed using a hydroalcoholic (hydroethanolic) extraction solvent (i.e. a hydroalcoholic (hydroethanolic) extract), wherein the extract comprises from about 1% to about 100% by weight, such as from about 1% to 95% by weight, or 2 to 90% by weight or 2% to about 80% or from about 5% to about 70% or from about 8% to about 65% by weight of one or more phlorotannins based on the dry weight of the extract, wherein the one or more phlorotannins have from about 10 to about 30 phloroglucinol units or from about 10 to about 23 phloroglucinol units and have an average molecular mass of 1000 g/mol or greater, such as from about 1000 g/mol to about 3000 g/mol or from about 1200 g/mol to about 2500 g/mol, for example, wherein at least about 70% by weight based on the dry weight of the phlorotannins in the dry extract have a molecular mass of from about 1000 g/mol to about 3000 g/mol based on the dry weight of the extract, and may comprise no polysaccharides derived from or derivable from seaweed (ie: be free of polysaccharides) or comprises a small amount of polysaccharides derived from or derivable from seaweed (ie: be substantially free of polysaccharides), for example from about 0% to about 10%, such as from about 0% to about 5%, such as from about 0% to about 1% based on the dry weight of the extract.

The extraction process used to obtain that extract of the invention may comprise two or more extraction steps. For example, the seaweed may be subjected to a hydroalcoholic extraction, such as a hydroethanolic extraction to produce a crude extraction product. This crude extraction product may then be subjected to one or more further extraction steps. In these further steps the same hydroalcoholic solvent may be used or a different hydroalcoholic solvent may be used (for example the ratio of the alcohol to the water may be varied) or an organic solvent such as ethyl acetate may be used as the solvent. If necessary, the crude extract may be dried to remove the extraction solvent between the extraction steps.

As an example, hydroethanolic extraction may be followed by extraction with ethyl acetate. The crude extract obtained after the hydroethanolic extraction may be dried before extraction with ethyl acetate.

Unless otherwise stated herein, the weight percentages listed are based on the total weight of extract obtained in dry form. For example, in some aspects, the weight percentages listed are based on the total weight of the dry extract. The extract may be a solid or a liquid.

The term "dry" used herein, e.g. when referring to the extract of the invention, refers to either a solid or liquid extract that is absent of solvent, for example the solvent used in the extraction, so that at least 95% of the solvent has been removed, such as via evaporation.

For the avoidance of doubt, preferences, options, particular features and the like indicated for a given aspect, feature or parameter of the invention should, unless the context indicates otherwise, be regarded as having been disclosed in combination with any and all other preferences, options, particular features and the like as indicated for the same or other aspects, features and parameters of the invention.

The term "about" used herein, e.g. when referring to a measurable value (such as an amount or weight of a particular component in the reaction mixture), refers to variations of ±20%, ±10%, ±5%, ±1%, ±0.5%, or, particularly, ±0.1% of the specified amount.

The skilled person will understand that the phlorotannins of the present invention and/or the extract of the invention (once the extraction solvent has been removed) may be provided in solid form or in liquid form, such as an oil. By solid form, it is included that the phlorotannins of the present invention and/or the extract may be provided as an amorphous solid, or as a crystalline or part-crystalline solid.

The phlorotannins of the present invention and/or the extract of the invention may be obtained or obtainable from at least one type of seaweed by extraction processes as generally described below, or routine modifications thereof.

The extraction process used to obtain the phlorotannins of the present invention and/or the extract of the invention comprises contacting the seaweed with an extraction solvent. Suitable extraction solvents are described above.

Suitable solvents include water, alcohol, alcohol/water mixtures (hydro-alcoholic solvents), ethyl acetate, acetone, hexane or any other solvent that may typically be used for extraction, and mixtures thereof. For example, the solvent may be 10%, 20%, 30%, 40%, 50%, 60%, 70%, 80%, or 90% alcohol in water, such as 60% alcohol in water (based on the total amount of solvent used, including any water present in the seaweed, of fresh seaweed is used). Particular alcohols that may be mentioned include ethanol (EtOH, hydro-ethanolic) and methanol (MeOH, hydro-methanolic). For example, the solvent may be from about 10% alcohol in water to about 90% alcohol (i.e. ethanol) in water, such as from about 20% to about 80% or from about 30% to about 70% or 40% to about 60%.

The temperature of the contacting (extraction) step will depend on the solvent used and may be in a range of from about 10° C. to about 50° C. For example, the temperature for extraction may be in a range of from about 20° C. to about 40° C. or from about 15° C. to about 25° C., eg about 20° C.

Extraction can be enhanced using any suitable method known in the art. For example, the contacting (extraction) of the seaweed may be performed with or without agitation, such as by stirring, for example, using an overhead stirrer. Alternatively, pressing can be used; for example, the seaweed can be placed in a press.

The contacting (extraction) period (i.e. the period during which the seaweed material is in contact with the solvent) is typically from about 0.5 hours to about 24 hours, such as from about 1 hour to 18 or 12 or 10 hours.

For example, on a laboratory scale, the seaweed may be contacted with the extraction solvent in an opaque large beaker and agitated using an overhead stirrer for approximately 5 hours at room temperature (15 to 25° C.) and atmospheric pressure.

As an example, on a larger scale, the seaweed may be contacted with the extraction solvent in an opaque milk tank and agitated with an overhead stirrer for approximately 17 hours at room temperature (15 to 25° C.) and atmospheric pressure.

The contacting (extraction) of the seaweed may be performed at atmospheric pressure or at a pressure above or below atmospheric pressure. Typically, the contacting (extraction) is conducted at atmospheric pressure.

Any suitable extraction apparatus may be used. The extraction apparatus may be opaque or covered, for example, in tin foil, in order to protect the extract from light, since phlorotannin are known to be sensitive to light.

The ratio of solvent to seaweed material can vary within wide limits. Typically, the ratio of solvent to seaweed material used in the extraction process ranges from about 1:1 to about 10:1 on a millilitre to gram basis, such as from about 2:1 to 5:1 e.g. 3:1 w/v.

The contacting (extraction) step may be then repeated as deemed necessary. For example, the contacting step may be repeated two, three or four times, i.e. the contacting step may be repeated at least three times.

One or more of the following optional steps may take place before the seaweed is contacted with the extraction solvent:
(a) washing the seaweed; and/or
(b) cutting the seaweed roughly into smaller pieces; and/or
(c) chopping the seaweed using rotating sharp blades, commonly known as a blender, at low speed into smaller particle sizes.

The seaweed that may be used to obtain phlorotannins of the present invention and/or an extract of the present invention may be frozen, freeze-dried, fresh, or dried. Preferably a fresh seaweed is used. If the seaweed has been dried or freeze-dried it is preferably rehydrated before use.

In step (a), the seaweed may be washed with an aqueous solvent, such as seawater, drinking water and/or distilled water, which may remove sand and stones and other dirt from the seaweed sample. Washing with seawater, followed by washing with drinking water or distilled water may be used.

In step (b), the seaweed may be roughly chopped into pieces using a chopping apparatus, such as scissors or a knife or mechanical chopping means. The seaweed may be chopped into particles of with an area in a range from about 1 $cm^2$ to 5 $cm^2$.

In step (c), the seaweed may be further chopped into particles of with an area in a range from about 1 $mm^2$ to 4 $mm^2$, such as from about 1.5 $mm^2$ to 3.5 $mm^2$, such as from about 2 $mm^2$ to 3 $mm^2$. Any suitable blending technique known in the art may be used, such as a blender.

Typically, steps (b) and (c) can be conducted as follows:
On small scale samples (e.g. <1 Kg of seaweed, such as fresh seaweed) by first cutting with scissors and then using a blender such as a Waring blender at low speed;

For larger industrial scale samples (e.g. >50 Kg of seaweed, such as fresh seaweed) by milling in a grinder such as an Urschel grinder in two stages (for example: Coarse grinding with 66708 grid, followed by fine grinding with 66896 grid).

Prior to the extraction step, the dry mass and the water content of the seaweed may be determined by drying the seaweed in an oven to obtain a constant weight, e.g. for approximately 24 hours and 103° C. This information can be used to determine the amount of solvent needed, for example the amount of water needed in a hydroalcoholic solvent, One or more of the following optional steps may take place after the seaweed has been contacted with the extraction solvent:
(e) separating the seaweed particles from the solvent; and/or
(f) evaporating the solvent; and/or
(g) purifying the crude extract.

After the contacting (extraction step) the sample may be left to settle, for example for up to 1 hour, for example for approximately 30 minutes.

Any un-dissolved plant material may be removed from the solvent, for example, by filtration, and re-dissolved in the solvent.

In step (e), the solvent may be separated from any un-dissolved seaweed material (for example, by filtration) and in step (f) the solvent (filtrate) concentrated (i.e. the solvent is removed). For example, the solvent may be concentrated until all the solvent has been removed and only solid extract remains.

For example, on a laboratory scale, the mixture is then sieved using a Buchner filter. On a larger scale, a 300-micro sieve, eg SWECO, may for example be used.

In step (f), the solvent (filtrate) may be concentrated (for example, by rotary evaporation at low temperature such as from about 35 to about 45° C., on a laboratory scale or using a Brouillon Process evaporator on a larger scale) to about 90% to 99% DM (Dry Material, Dried Matter or Dry Matter).

In step (g), the crude extract may be further purified to provide a purified extract of the invention. Any suitable purification method known in the art may be used. Examples of suitable methods include chromatography techniques such as reversed phase liquid chromatography, filtration methods such as tangential flow filtration (TFF) or ultrafiltration, and/or further extractions steps as discussed above, such as solid phase extraction (SPE). As an example, the crude extract may be passed through a 1000 g/mol ultrafiltration membrane, this may remove compounds with a molecular weight below 1000 g/mol.

As an example, the extract of the invention may be obtained using a process as follows:
(a) washing the seaweed;
(b) optionally cutting the seaweed roughly into smaller pieces;
(c) optionally chopping the seaweed using rotating sharp blades, commonly known as a blender, at low speed into smaller particle sizes;
(d) contacting the seaweed particles with a solvent;
(e) separating the seaweed particles from the solvent;
(f) evaporating the solvent; and
(g) optionally purifying the crude extract.

By the process of extraction, the percentage of certain active compounds within the extract are increased and other compounds decreased when compared to the percentage of active compounds found in the originating plant.

The phlorotannins of the present invention and/or the extract of the invention as may be an extract obtained from (or obtainable by) a process of the invention as previously described.

The extract of the invention may be freeze dried. For example, the freeze-dried extract may be obtained by freezing the extract in shallow trays at a temperature of from about −10 to −50° C., such as about −36° C., followed by freeze drying with Condenser temperature of about −50 to −100° C., eg about −87° C. and Pressure 200-400 mTorr for up to 3 days depending on the size of the sample.

The phlorotannins of the present invention and/or the extract may be ground to a powder.

The phlorotannins of the present invention and/or the extract of the invention may be stored in any suitable manner. For example, the phlorotannins of the present invention and/or the extract (for example in the form of a powder), may be frozen and protected from moisture, heat and light to avoid deterioration.

The phlorotannins of the present invention and/or the extract of the invention may be provided in the form of a composition. Such compositions described herein may be prepared according to methods known to those skilled in the art, such as by bringing the components of the composition into admixture.

The amount of the phlorotannins of the present invention and/or the extract present in a composition comprising the extract of the invention will depend on the intended use, and the other components present in the composition.

When included within a composition, the phlorotannins of the present invention and/or the extract is typically present in an amount from about 0.01% by weight to about 100% by weight, for example, from about 0.1% by weight to about 90% by weight or from about 10% by weight to about 80% by weight or from about 5% by weight to about 70% or from about 40% by weight to about 60% by weight based on the total weight of the composition.

At the point of use or application, the concentration of phlorotannins of the present invention and/or extract of the invention in a composition may, for example be from about 0.01 to about 100%; such as from about 0.1 to about 50%; or from about 0.5 to about 20%; or from about 1% to about 10% by weight based on the total weight of the composition. A composition could be prepared in a ready-to-use form or could be made in a more concentrated form that would be diluted prior to use according to a recommended dilution factor, such as 1:100, 1:50; 1:20; 1:10 or 1:5. to achieve the required concentration at the point of use.

When phlorotannins of the present invention and/or extract of the invention is included in a composition, the composition typically comprises phlorotannins in an amount of about 0.0025% to about 50% by weight of the composition, such as from 0.025 or 0.1% to 25% by weight of the composition, for example 1 to 10% by weight of the composition.

At the point of use or application, the concentration of phlorotannins in a composition may, for example be from about 0.0025 to about 25%; such as from about 0.025 to about 15%; or from about 0.1 to about 5%; or from about 0.25% to about 2.5% by weight based on the total weight of the composition. A composition could be prepared in a ready-to-use form or could be made in a more concentrated form that would be diluted prior to use according to a recommended dilution factor, such as 1:100, 1:50; 1:20; 1:10 or 1:5. to achieve the required concentration at the point of use.

For avoidance of doubt, in this specification when we use the term "comprising" or "comprises" we mean that the extract or composition being described must contain the listed ingredient(s) but may optionally contain additional ingredients. When we use the term "consisting essentially of" or "consists essentially of" we mean that the extract or composition being described must contain the listed ingredient(s) and may also contain small (for example up to 5% by weight, or up to 1% or 0.1% by weight) of other ingredients provided that any additional ingredients do not affect the essential properties of the extract or composition. When we use the term "consisting of" or "consists of" we mean that the extract or composition being described must contain the listed ingredient(s) only. These terms can be applied in an analogous manner to processes, methods and uses.

The extract of the present invention and/or compositions comprising the extract of the present invention may be used as an anti-viral agent.

By the term "anti-viral" we mean a compound or composition that destroys and/or renders the virus non-viable and/or inhibits the replication of the virus.

Viruses can be classified based on the genomic nature of the viruses. This system is known as the Baltimore system of virus classification. In this system, there are seven groups:

I. Double-Stranded DNA Viruses

Some replicate in the nucleus e.g adenoviruses using cellular proteins. Poxviruses replicate in the cytoplasm and make their own enzymes for nucleic acid replication. e.g. adenoviruses; herpesviruses; poxviruses, etc II. Single-Stranded (+) Sense DNA Viruses Replication occurs in the nucleus, involving the formation of a (−) sense strand, which serves as a template for (+)strand RNA and DNA synthesis. e.g., parvoviruses III. Double-Stranded RNA Viruses These viruses have segmented genomes. Each genome segment is transcribed separately to produce monocistronic mRNAs. e.g., reoviruses IV. Single-Stranded (+) Sense RNA Viruses (Picornaviruses; Togaviruses, Etc)

Polycistronic mRNA: Genomic RNA can function as mRNA. Since the RNA is the same sense as mRNA, the RNA alone is infectious, no virion particle associated polymerase. Translation results in the formation of a polyprotein product, which is subsequently cleaved to form the mature proteins. e.g. picornaviruses (poliovirus, rhinovirus); hepatitis A virus Complex Transcription: Two or more rounds of translation are necessary to produce the genomic RNA. e.g. picornaviruses; hepatitis A virus.

V. Single-Stranded (−) Sense RNA Viruses

The virion RNA is negative sense (complementary to mRNA) and must therefore be copied into the complementary plus-sense mRNA to make proteins. This group of viruses must code for RNA-dependent RNA-polymerase and also carry it in the virion so that they can make mRNAs upon infecting the cell. e.g. orthomyxoviruses, rhabdoviruses, etc Segmented e.g. orthomyxoviruses. First step in replication is transcription of the (−) sense RNA genome by the virion RNA-dependent RNA polymerase to produce monocistronic mRNAs, which also serve as the template for genome replication.

Non-segmented e.g. rhabdoviruses. Replication occurs as above and monocistronic mRNAs are produced.

VI. Single-Stranded (+) Sense RNA Viruses with DNA Intermediate in Life-Cycle

RNA genome is (+) sense but unique among viruses in that it is DIPLOID, and does not serve as mRNA, but as a template for reverse transcription. e.g. retroviruses.

Retroviruses therefore encodes an RNA-dependent DNA polymerase (reverse transcriptase) to make the DNA provirus which then is transcribed to genomic RNA by a host enzyme, RNA polymerase II.

VII. Double-Stranded DNA Viruses with RNA Intermediate

This group of viruses also relies on reverse transcription, but unlike the retroviruses, this occurs inside the virus particle on maturation. On infection of a new cell, the first event to occur is repair of the gapped genome, followed by transcription. e.g., hepadnaviruses An extract or composition of the present invention may be used as an anti-viral agent against viruses in all seven groups or the extract of the present invention may be used as an anti-viral agent against viruses in one or more groups. For example, the extract of the invention may be used as an anti-viral agent against viruses in one or more of group I (such as adenovirus), group II (such as parvovirus), group III (such as rotavirus), group IV (such as poliovirus and norovirus), group V (such as influenza A H1N1 virus), group VI or group VII. For example, the extract of the invention may be used as an antiviral agent against viruses of one or more of group I, II, III or V.

The extent to which a compound or composition destroys and/or renders the virus non-viable can be measured using the test method BS EN 14476:2013+A1:2015

Chemical disinfectants and antiseptics—Quantitative suspension test for the evaluation of viricidal activity in the medical area. Test method and requirements (Phase 2/Step 1) have been defined as a standard European Test Method within the Biocidal Products Regulation (BPR). Full details of this method can be found in the regulation.

A summary now follows which will be understand by a person skilled in the art: A sample of the compound or composition to be tested is added to a test suspension of viruses in a solution of an interfering substance. The mixture is maintained at one of the temperatures and the contact times specified in Clause 4 and 5.5.1.1. At the end of this contact time, an aliquot is taken; the viricidal action in this portion is immediately suppressed by a validated method (dilution of the sample in ice-cold cell maintenance medium). The dilutions are transferred into culture units (petri dishes, tubes or wells of microtitre plates) either using monolayer or cell suspension. Infectivity tests are done either by plaque test or quantal tests. After incubation, the titres of infectivity are calculated according to Spearman and Karber (quantal tests, C.1) or by plaque counting (plaque test, C.2) and evaluated. Reduction of virus infectivity is calculated from differences of log virus titres before (Virus control) and after treatment with the product.

For the purposes of the current invention a compound or composition is considered to render a virus non-viable or inhibit the replication of the virus if it achieves a log reduction (after treatment vs before treatment) as described above of at least 1.0, preferably at least 2.0, more preferably at least 3.0, even more preferably at least 4.0, even more preferably to completely eliminate the virus.

The phlorotannins or an extract of the present invention and/or compositions of the present invention may be used against enveloped and/or non-enveloped viruses.

For example, the phlorotannis or an extract of the present invention and/or compositions of the invention may be used to reduce the activity or kill at least one of enveloped viruses selected from the families Herpesviridae, Poxviridae, Hepadnaviridae, Coronaviridae, Flaviviridae, Togaviridae, Retroviridae, Orthomyxoviridae, Arenaviridae, Bunyaviridae, Filoviridae, Paramyxoviridae, and Rhabdoviridae.

The phlorotannins or an extract of the present invention and/or compositions of the invention may be used to reduce actively or kill at least one of enveloped viruses selected from herpes simplex type 1, herpes simplex type 2, varicella-zoster virus, Esptein-Barr virus, human cytomegalovirus, human herpesvirus type 8, variola virus, hepatitus B virus, severe acute respiratory syndrome virus, hepatitis C virus, yellow fever virus, dengue virus, West Nile virus, TBE virus, rubella virus, human immunodeficiency virus, influenza virus, lassa virus, Crimean-Congo haemorrhagic fever virus, hantaan virus, ebola virus, Marburg virus, measles virus, mumps virus, parainfluenza virus, respiratory syncytial virus, and rabies virus.

The phlorotannins or an extract of the present invention and/or compositions of the invention may be used against at least one of the non-enveloped viruses selected from the families Adenoviridae, Papillomaviridae, Polyomaviridae, Parvoviridae, Astroviridae, Caliciviridae, Picornaviridae, Hepeviridae, and Reoviridae.

The phlorotannins or an extract of the present invention and/or compositions of the inventions may be used against at least one of the non-enveloped viruses selected from adenovirus, human papillomavirus, BK virus, JC virus, parvovirus B19, human astrovirus, coxsackievirus, hepatitis A virus, poliovirus, rhinovirus, hepatitis E virus, rotavirus, orbivirus, coltivurs, norovirus and Banna virus.

Thus, the present invention provides an extract or composition as previously defined for use as an anti-viral agent.

The phlorotannins or an extract of the present invention and/or compositions of the inventions may be used to treat or prevent viral infection, such as viral infection in of an animal or plant.

These is also provided the use of an extract or composition as previously defined in the manufacture of a medicament for treating or preventing a viral infection.

There is also provided a method of treating or preventing a viral infection comprising the administration of a therapeutically effective amount of an extract or composition as defined previously to a subject in need thereof, such as a subject who has been infected with a virus or a subject who will or may come into contact with a virus.

Thus, there is also provided the use of an extract or composition as previously defined as an anti-viral agent.

Viruses may be present in vivo or outside living organisms. The present invention may be used to reduce or control the virus on or at a surface.

The present invention also provides the use of a phlorotannin comprising an average of from about 10 to about 23 phloroglucinol units as an anti-viral agent.

The present invention also provides a phlorotannin comprising an average of from about 10 to about 23 phloroglucinol units for use as an anti-viral agent.

The present invention also provides an anti-viral composition comprising a phlorotannin comprising an average of from about 10 to about 23 phloroglucinol units.

The present invention also provides a composition comprising a phlorotannin comprising an average of from about 10 to about 23 phloroglucinol units for use as an anti-viral agent.

The present invention also provides the use of a composition comprising a phlorotannin comprising an average of from about 10 to about 23 phloroglucinol units as an anti-viral agent.

Phlorotannins comprising an average of from about 10 to about 23 phloroglucinol units may be used against the viruses mentioned herein.

The present invention also provides an anti-viral composition comprising one or more phlorotannins. In particular, an anti-viral composition comprising one or more phlorotannins having a molecular mass of from about 1000 g/mol to about 3000 g/mol.

The present invention also provides a composition comprising one or more phlorotannin for use as an anti-viral composition, for example for use to treat or prevent viral infections. In particular, a composition comprising one or more phlorotannin having a molecular mass of from about 1000 g/mol to about 3000 g/mol for use as an anti-viral composition, for example for use to treat or prevent a viral infection.

The present invention also provides the use of a composition comprising one or more phlorotannins as an anti-viral composition. In particular, the use of a composition comprising one or more phlorotannins having a molecular mass of from about 1000 g/mol to about 3000 g/mol as an anti-viral composition.

As detailed above, the phlorotannins may be obtained using water, alcohol, organic solvents or mixtures thereof.

The phlorotannins present in the compositions described herein may be obtained or obtainable from brown seaweeds as described previously, and may be used as an anti-viral composition or agent as described previously.

It will be appreciated that the compositions of the invention can comprise other ingredients commonly used in the art. The nature of any other ingredients used will depend on the nature and intended purpose of the composition. The person of ordinary skill in the art will know which additional ingredients are suitable for use in compositions for different applications. Additional ingredients that may be used in the compositions of the invention include but are not limited to—buffering agents, pH modifiers, complexing agents, surfactants, solvents (such as water). The compositions of the invention may also contain other ingredients that are standard in the art such as colorants, fragrances, emollients, antioxidants, thickeners and corrosion inhibitors and mixtures thereof.

Figure 1A:
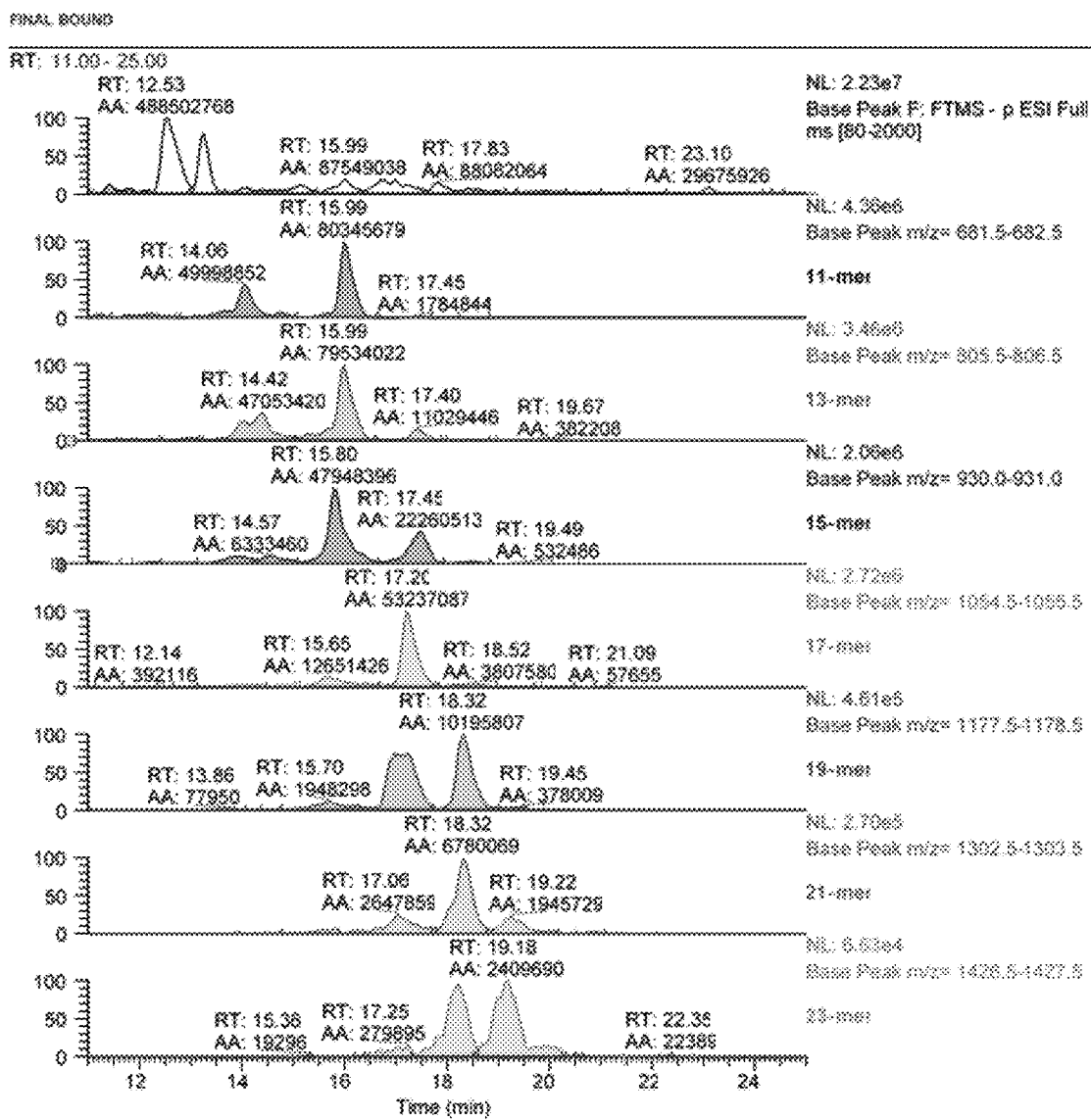
FIG. 1a shows the peak areas of phlorotannin oligomers having an odd number of repeating units in the extract of Example 3.

The invention is illustrated by the following non-limiting Examples.

Example 1—Small Scale Preparation of an Extract of the Invention

Fresh *Ascophyllum nodosum* (brown seaweed) which was sourced from Ireland having been harvested in January 2016 was used.

The water content of the fresh seaweed was determined as follows:

The moisture content of the seaweed was determined by drying a known weight of the seaweed in an oven to constant weight for approximately 24 hours at 103° C.

The seaweed was weighed, and the dry mass of the seaweed determined. The corresponding mass of water contained in the fresh seaweed was determined by subtracting the dry mass of the seaweed from the mass of the fresh seaweed, the percentage water is the fresh seaweed was then determined. For this seaweed, it was determined that the fresh seaweed was 70% water (ie 1000 g of seaweed contained 700 g of water).

An extract of the invention was prepared as follows:

1000 g of the seaweed was used. This was pre-washed with seawater to remove any debris such as sand and stones. The seaweed was then washed with freshwater.

The seaweed was cut into pieces approximately 2-3 mm in diameter. This was done by first cutting with scissors and then using a Waring blender at low speed.

An Ethanol/Water blend was added to the seaweed. The ethanol used was 96% pure ethanol and 4% water. The amount of ethanol and water used in this ethanol/water blend satisfied the following two criteria:

The ratio of the masses of ethanol in the blend to the total water present (i.e. water contained in the seaweed+the water in the blend+any additional water added in the blend) is 60:40

The total mass of the water and ethanol was three times the mass of the fresh seaweed to which it is added The mass of water added as part of the ethanol/water blend to meet the above criteria can be determined through simple mathematics.

In this example, 1000 g of fresh seaweed is used and 700 g of this was determined to be water and 300 g the dry seaweed.

The total mass of the Ethanol and Water is 3000 g (i.e. 3×1000 g). And this is in an Ethanol: water ratio of 60:40. So 1875 g of Ethanol (considering the ethanol used is 96% ethanol and 4% water), and 1125 g of water. 700 g of this water is already contained in the fresh seaweed, so an additional 425 g of water is to be added as the Ethanol/water blend.

The Ethanol/Water blend was added to the washed, fresh seaweed in a large opaque beaker.

The mixture was agitated using an overhead stirrer for approximately 5 hours at room temperature.

After this time the sample was left to settle for approximately 30 minutes.

The mixture was then sieved using a Buchner filter.

The alcohol was then evaporated at low temperature (34-45° C.) using a rotary evaporator.

The extract was then frozen at −36° C. in shallow trays to maximize the surface area.

The extract was then freeze dried with Condenser temperature of −87° C. and Pressure 200-400 mTorr for approximately 3 days.

The extract was then ground to create a powder.

The powder extract was then frozen and protected from moisture, heat and light to avoid deterioration.

It was thawed as needed prior to testing.

Example 2—Antiviral Testing

Seaweed extracts obtained in Example 1 were used.

The thawed seaweed extract was dissolved in demineralised water to the required concentration for testing.

The extent to which a compound or composition renders the virus non-viable or inhibits the replication of the virus was measured using the test method BS EN 14476:2013+A1:2015 Chemical disinfectants and antiseptics—Quantitative suspension test for the evaluation of viricidal activity in the medical area. Test method and requirements (Phase 2/Step 1) have been defined as a standard European Test Method within the Biocidal Products Regulation (BPR). Full details of this method can be found in the regulation.

Using this method, the log reduction value for the particular virus the extract solution was being tested against was determined.

The contact time is the time that the test solution was in contact with the test virus during the test. The results are shown in Table 1 below.

TABLE 1

| Example (CC3687; BYO2) | Concentration of Extract tested in water | Virus | Contact Time | $Log_{10} R^*$ |
|---|---|---|---|---|
| 2-A | 2% | Norovirus | 60 min | ≥4.38 |
| 2-B | 2% | H1N1 | 60 min | ≥2.63 |
| 2-C | 2% | Rotavirus | 60 min | ≥3.75 |
| 2-D | 2% | H1N1 | 60 min | ≥4.00 |
| 2-E | 2% | H1N1 | 2 min | ≥4.00 |
| 2-F | 2% | Norovirus | 60 min | ≥4.88 |
| 2-G | 2% | Norovirus | 2 min | ≥4.63 |
| 2-H | 2% | Rotavirus | 60 min | ≥5.44 |
| 2-I | 2% | Rotavirus | 2 min | ≥5.44 |
| 2-J | 2% | H1N1 | 60 min | ≥4.00 |
| 2-K | 2% | H1N1 | 2 min | ≥4.00 |
| 2-L | 2% | Poliovirus | 60 min | 4.67 |
| 2-M | 2% | Poliovirus | 2 min | 4.50 |
| 2-N | 2% | Adenovirus | 60 min | 4.83 |
| 2-O | 2% | Adenovirus | 2 min | 4.66 |
| 2-P | 2% | H1N1 | 60 min | ≥5.00 |
| 2-Q | 2% | H1N1 | 2 min | ≥5.00 |
| 2-R | 2% | Norovirus | 60 min | ≥4.75 |
| 2-S | 2% | Norovirus | 2 min | ≥4.50 |
| 2-T | 2% | H1N1 | 60 min | ≥5.00 |
| 2-U | 2% | H1N1 | 2 min | ≥5.00 |
| 2-V | 2% | Rotavirus | 60 min | ≥5.44 |
| 2-W | 2% | Rotavirus | 2 min | ≥5.44 |
| 2-X | 2% | Norovirus | 60 min | ≥4.85 |
| 2-Y | 2% | Norovirus | 2 min | ≥4.60 |

*where the $Log_{10}R$ value shows a ≥ sign it implies that complete elimination of the virus has occurred. H1N1 indicates influenza A virus subtype H1N1.

Example 3—Larger Scale Preparation of an Extract of the Invention

Fresh *Ascophyllum nodosum* (brown seaweed) which was sourced from Brittany in France having been harvested in November 2017.

The water content of the fresh seaweed was determined as follows:

The moisture content of the seaweed was determined by drying a known weight of the seaweed in an oven to constant weight for approximately 24 hours at 103° C.

The seaweed was weighed, and the dry mass of the seaweed determined. The corresponding mass of water contained in the fresh seaweed was determined by subtracting the dry mass of the seaweed from the mass of the fresh seaweed, the percentage water is the fresh seaweed was then determined.

69 Kg of fresh *Ascophyllum nodosum* (brown seaweed) was used. The harvested seaweed was soaked overnight in seawater. The next day it was hand-sorted to remove epiphytic seaweed attached to the *Ascophyllum* biomass and drained for 30 minutes. It was then rinsed with freshwater for 3 minutes and drained again.

The seaweed was then milled in an Urschel grinder in two steps (Coarse grinding with 66708 grid, followed by fine grinding with 66896 grid). This produced 2-3 mm particles.

An Ethanol/Water blend was added to the seaweed. The ethanol used was 96% pure ethanol and 4% water. The amount of ethanol and water used in this Ethanol/water blend satisfied the following two criteria:

The ratio of the masses of ethanol in the blend to the total water present (i.e. water contained in the seaweed+the water in the blend+any additional water added in the blend) is 60:40 The total mass of the water and ethanol was three times the mass of the fresh seaweed to which it is added The mass of water added to the Ethanol/water blend to meet the above criteria is determined through simple mathematics.

In this example, 69 Kg of fresh seaweed is used and 52 Kg of this was determined to be water and 17 Kg the dry seaweed.

The total mass of the Ethanol and Water is 207 Kg (i.e. 3×69 Kg). And this is in an Ethanol: water ratio of 60:40. So 129.4 Kg of Ethanol (considering the ethanol used is 96% ethanol and 4% water), and 77.6 Kg of water. 52 Kg of this water is already contained in the fresh seaweed, so an additional 25.6 Kg of water is to be added as the Ethanol/water blend.

The extraction was performed in an agitated milk tank, for 17 hours at room temperature and pressure.

The spent biomass was separated from the extract on a 300 μm sieve (SWECO).

The alcohol was evaporated at low temperature in a Brouillon Process evaporator (initial temperature 34° C., final temperature 45° C.), taking approximately 8 hours.

The extract was further clarified using filtration aid FW12 (diatomaceous earth) and KDS12 filters (cellulose-based depth filter sheets) mounted on a Millipore frame.

The resulting filtered extract was transferred to polypropylene trays and freeze dried using a slow-cycle (25-30 Kg.prg) to avoid inhomogeneous freezing. This took approximately 3 days.

The extract was then grinded using a lab scale blender. 2.92 Kg of powdered extract resulted.

The powder extract was then frozen and protected from moisture, heat and light to avoid deterioration.

It was thawed as needed prior to testing.

The composition of the extract obtained was analysed.

A small sample of the extract was added to Folin-Ciocalteu's phenol reagent and the blue colour that developed after addition of sodium carbonate solution was assessed against a standard curve of gallic acid, as a standard phenolic compound.

This positive reaction with Folin-Ciocalteu's phenol reagent indicated the present of phlorotannins.

The nature of the phlorotannins was then investigated using liquid chromatography mass spectrometry techniques using an LC system with an LTQ Orbitrap XL mass spectrometer (Thermo Fisher Scientific). A neat sample of the extract was separated on a reversed phase C18 column and analysed in negative ESI mode (the method used is described in Austin et al. (2017) Extracts from the edible seaweed, *Ascophyllum nodosum*, inhibit lipase activity in vitro: Contributions of phenolic and polysaccharide components. Food & Function, 9, 502-510—DOI: 10.1039/C7FO01690E)

Figure 1B:
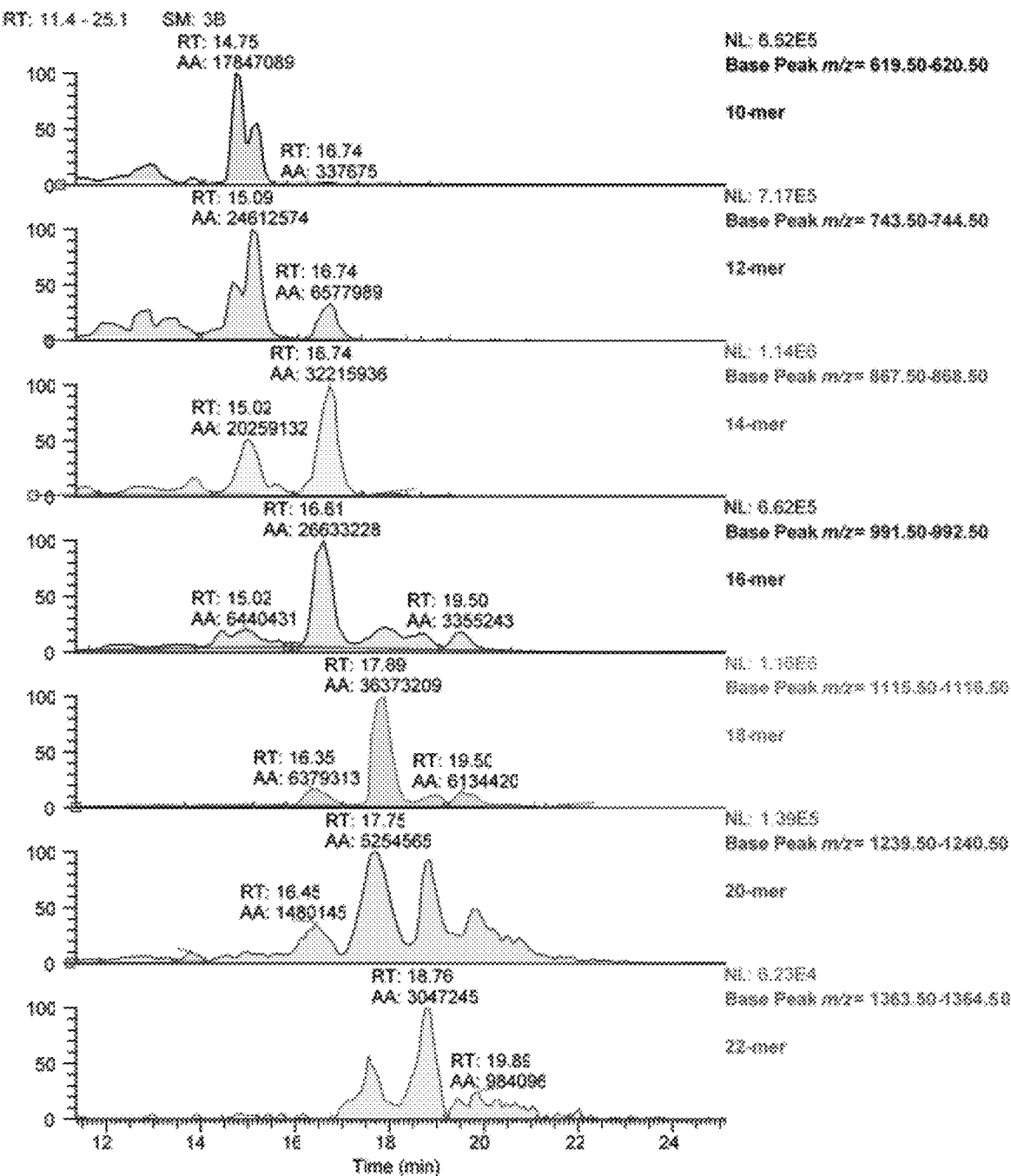
FIG. 1b shows the peak areas of phlorotannin oligomers having an even number of repeating units in the extract of Example 3.

A series of phlorotannin oligomers were detected with apparent degree of polymerisation (DP) of phloroglucinol units from 10 to 23. The detection of phlorotannins with masses indicative of oligomers of odd numbered DP is shown in FIG. 1a (e.g. 11-23 DP) and even numbered DPs in FIG. 1b. Generally, more than one isomer was present for each oligomer.

Figure 2:
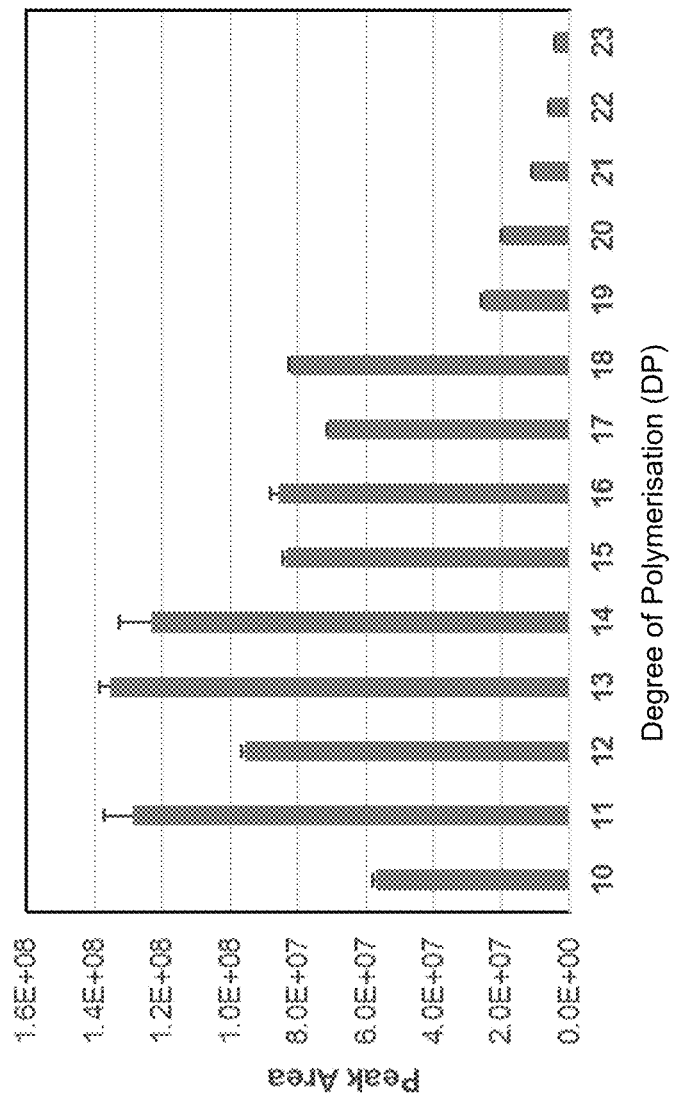
FIG. 2 shows the size distribution of the phlorotannin oligomers in the extract of Example 3.

The relative amounts of the PT oligomers were assessed by their MS peak areas (FIG. 2). There was a size distribution from DP 10 to 23 with the most abundant forms from DP11 to 18 and a sharp drop off in abundance from DP19 onwards.

Example 4—Antiviral Testing

Seaweed extracts obtained in Example 3 were used.

The thawed seaweed extract was dissolved in demineralised water to the required concentration for testing. The method for anti-viral testing described was used to determine the log reduction value for the particular virus the extract solution was being tested against. The contact time is the time that the test solution was in contact with the test virus during the test. The results are shown in Table 2 below.

TABLE 2

| Example | Concentration of Extract tested in water | Virus | Contact Time | $Log_{10} R$ |
|---|---|---|---|---|
| 4-A | 2% | Norovirus | 60 min | ≥4.47 |
| 4-B | 2% | Norovirus | 2 min | ≥4.35 |
| 4-C | 2% | Norovirus | 60 min | ≥4.47 |
| 4-D | 2% | Norovirus | 2 min | ≥4.35 |
| 4-E | 2% | Norovirus | 2 min | ≥4.63 |
| 4-F | 1% | Norovirus | 2 min | 3.13 |
| 4-G | 2% | Norovirus | 0.5 min | ≥4.50 |
| 4-H | 2% | Poliovirus | 60 min | ≥5.00 |
| 4-I | 2% | Poliovirus | 2 min | ≥5.50 |
| 4-J | 2% | Adenovirus | 60 min | ≥4.25 |
| 4-K | 2% | Adenovirus | 2 min | ≥4.25 |

*where the $Log_{10}R$ value shows a ≥ sign it implies that complete elimination of the virus has occurred.

Example 5—Purification of Crude (Hydroethanolic Extract) Using Solid Phase Extraction (SPE) to Separate into Two Fractions (i) More Hydrophilic Fraction: (ii) More Hydrophobic Fraction The extract (as obtained from Example 3) was freely soluble in ultra-pure water (UPW) containing 0.1% formic acid (FA) at 5% (w/w) and a 250 mL solution was prepared for use in the first test run (SPE-1). The SPE UNIT (Strata C18-E GIGA tube, 50 g capacity & 150 mL volume; Phenomenex Ltd) tube was prepared with 2 volumes of acetonitrile (ACN) containing 0.1% FA then equilibrated with 3 volumes of UPW containing 0.1% FA (Nwosu et al., 2011). The extract was applied in 60 mL batches and elution expedited using a side-arm flask and vacuum line.

After all of the extract sample solution was applied, the UNBOUND (hydrophilic) fraction was removed and the SPE unit washed with 2× volumes of UPW+FA, collected as the WASH fraction. Then the BOUND (hydrophobic) fraction was obtained by eluting the unit with 2 volumes of acetonitrile+FA. The unit could then be re-equilibrated for further use by washing with excess UPW+FA and stored in UPW+FA in the fridge until required.

For a second SPE (SPE-2) run, 400 mL of 5% (w/v) extract was prepared. The SPE procedure was the same apart from two changes. As the capacity of the SPE unit would be exceeded using this amount of material, the SPE procedure was repeated to re-capture any phenolic material that had passed into the UNBOUND fraction. Therefore, the BOUND fraction was composed of two combined fractions eluted from the unit. Also, the material that was eluted from the unit after removal of the bound fraction during the re-washing of the SPE unit was collected.

TOTAL CHOn and Phenolic Contents of Fractions

The total carbohydrate (CHOn) content of the BOUND and UNBOUND fractions were measured using the phenol-sulphuric acid method and the total phenol content (TPC) using the Folin-Ciocalteu method (Austin et al., 2017).

In SPE-1, the overall recovery of CHOn was 46.3% with 44.3% in the UNBOUND fraction and 2.0% in the BOUND fraction. The overall recovery of Total Phenol Content (TPC) was higher at 70.3% with the majority recovered in the BOUND fraction (56.8%) and less in the UNBOUND fraction (13.7%).

IN SPE-2, the overall recovery of CHOn was higher at 59.1% with 54.6% in the UNBOUND fraction and 4.5% in the BOUND fraction. However, the BOUND-WASH recovery fraction contained significant amounts of CHOn (i.e. 10.7% total) so the overall recovery of CHOn reached to 69.8%. That this "back-wash" fraction accounted for a fair amount of the "lost" CHOn in SPE-1 was unexpected given the chemistry of the SPE units.

For SPE-2, the TPC recovery figure reached 82.1% with the majority (70.0%) in the BOUND fraction and 12.1% in the UNBOUND fraction. The Bound Wash fraction accounted for a further 3.4% so the overall recovery of TPC reached 85.5%. It must be noted that neither of the two quantification methods is absolutely specific for CHOn or phenolics and therefore other components may interfere in their quantification.

Overall, the UNBOUND fraction was CHOn-rich and the TPC was poor whereas the BOUND fraction contained the majority of the TPC.

Expressed as a ratio of CHOn/TPC, the original extract had a value of −3.71 whereas the UNBOUND 1 ratio was 11.86 and the UNBOUND 2 was 17.24, which illustrates considerable enrichment in CHOn. The BOUND fraction 1 had a ratio of 0.136 and the BOUND fraction 2 had 0.255 which shows the enrichment of phenolics and removal of CHOn. The Bound Wash fraction was 12.04 also showing enrichment in CHOn.

Fractionation by Sephadex LH-20

A portion of the extract was fractionated using Sephadex LH20 using a technique (Pantidos et al., 2014) well-known to select for phlorotannin-like components (https://users.miamioh.edu/hagagermae/). A 25 mg/ml solution of the extract in UPW was produced and then 5 mL was added to 5 mL ethanol and mixed well. The extract was soluble in 50% ethanol and, in other tests, was fully soluble at up to 80% ethanol.

The extract solution was added to 5 mL of a slurry of Sephadex LH20 in 50% ethanol and mixed well for 10 mins at room temperature. After centrifugation at 2500 g for 5 mins at 5° C., the unbound fraction was removed and 5 mL of 50% ethanol added. The centrifugation procedure was repeated to give the WASH fraction then similarly with 50% acetone and then two washes with 80% acetone. The total CHOn and phenol contents were measured as before and 2×1 ml aliquots of each fraction were dried in a Speed-Vac for LC-MS analysis.

Figure 3:
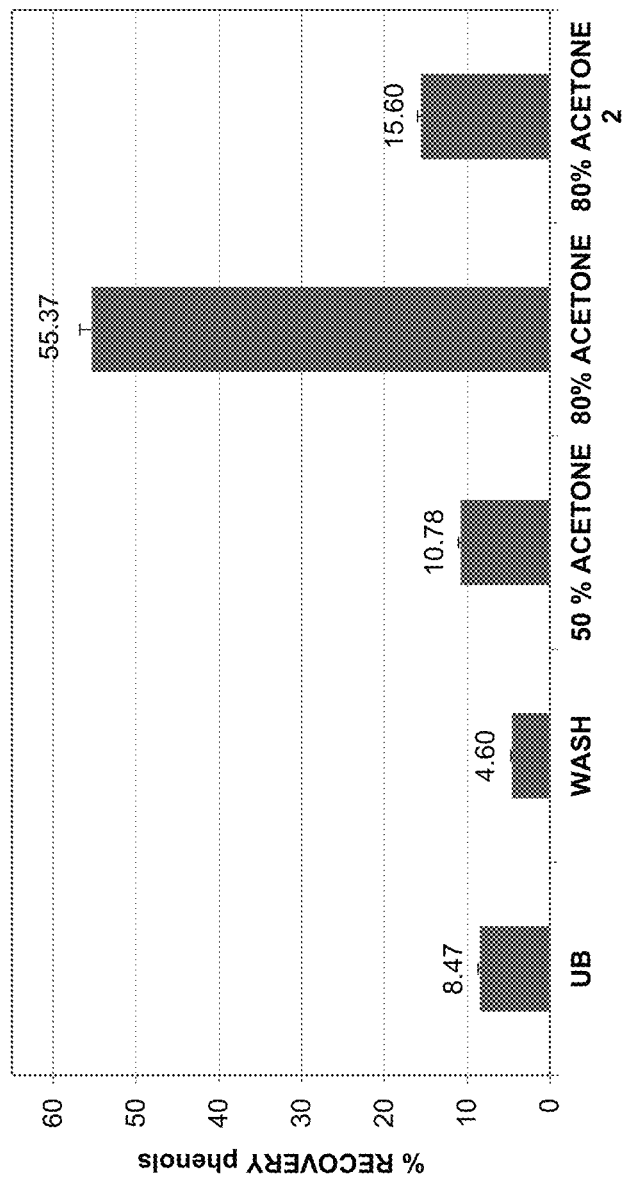
FIG. 3 shows the recovery of phenolics from LH20 fractionation in Example 5.

As shown in FIG. 3, the majority of the phenolic material was recovered in the first 80% acetone fraction with over 80% in the fractions released by acetone, which should be enriched in phlorotannin components.

Liquid Chromatography Mass Spectrometric (LC-MS) Analysis: Evidence for phlorotannins Samples of the BOUND and UNBOUD fractions were analysed using a previously described method (Pantidos et al., 2014; Nwosu et al., 2011) using electrospray ionisation MS in both positive and negative mode to examine the composition of the fractions. The components were separated on a C18 reverse phase column and the elution of phenolic material monitored at 280 nm. Initial LC-MS data was obtained using a Fleet MS then selected samples were re-analysed using an Orbitrap MS which gives higher sensitivity combined with facilities to give exact mass data and discrimination of multiply charged ions.

Figure 4:
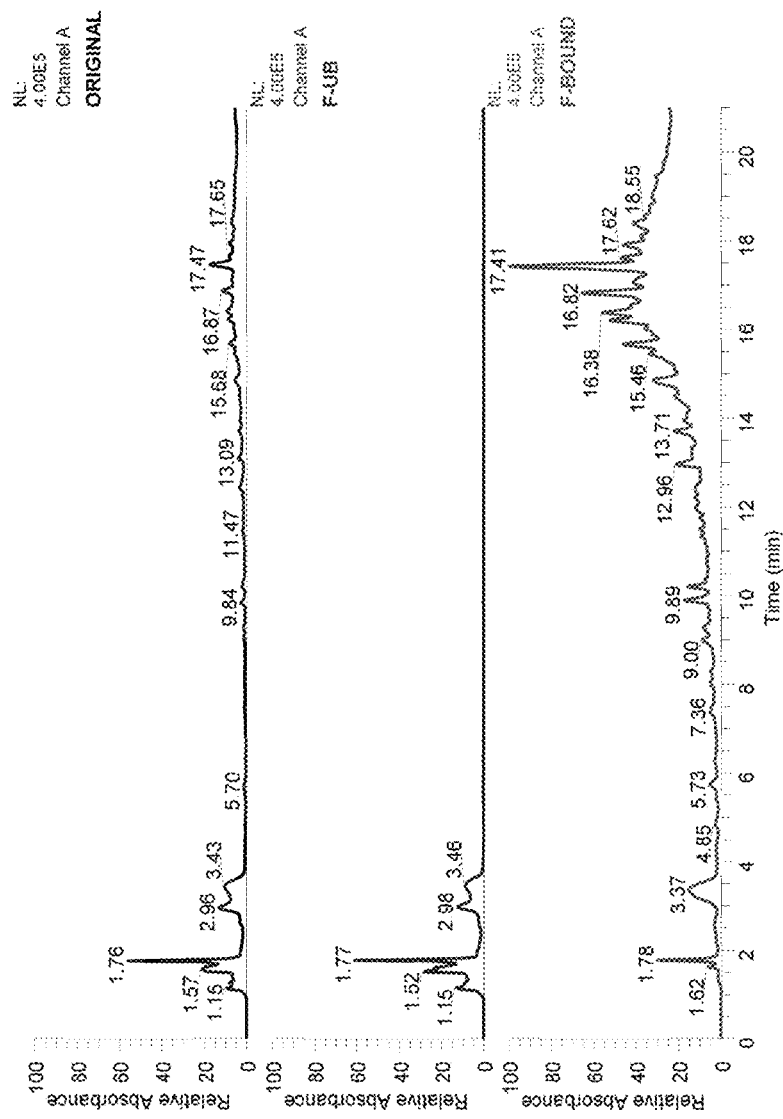
FIG. 4 shows the composition of the ORIGINAL, FUB and FUB fractions in Example 5.

As shown in FIG. 4, the BOUND sample was enriched in later eluting UV-absorbing peaks whereas the UNBOUND fraction was essentially devoid of these peaks.

Figure 5:
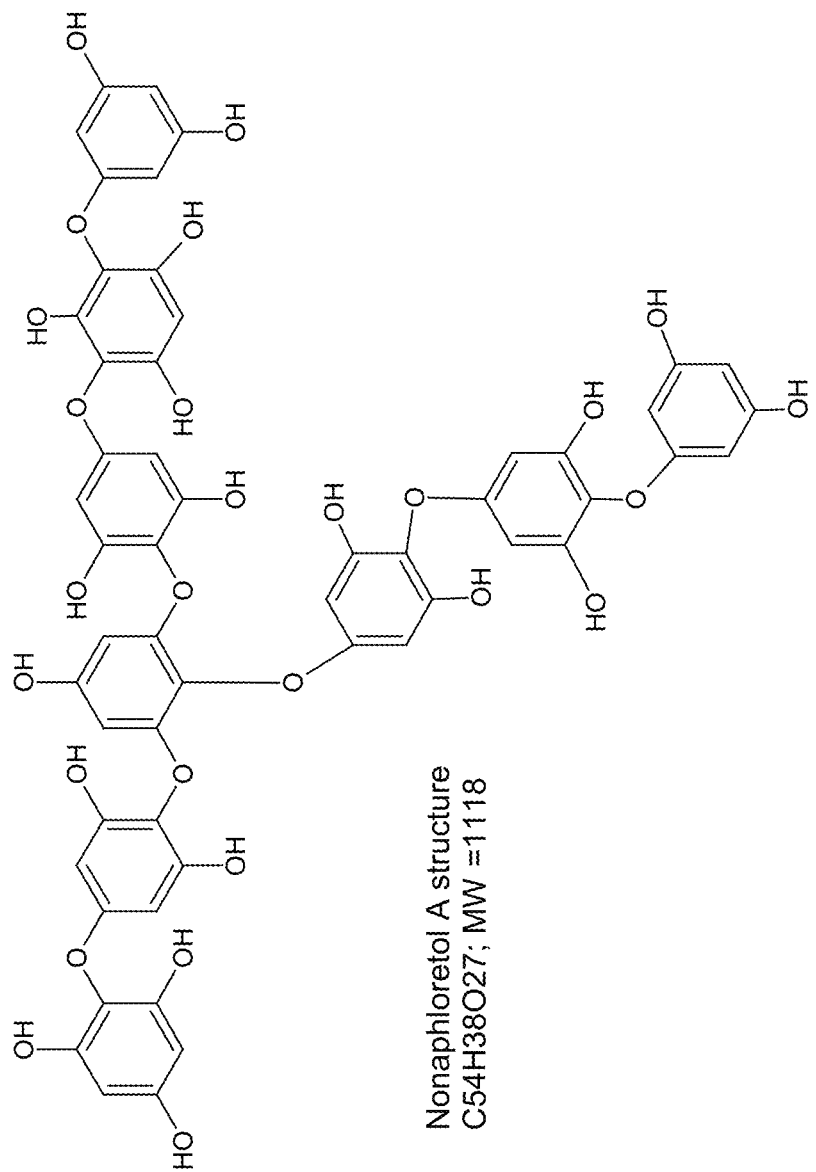
FIG. 5 shows the possible structure of m/z 1117 component in Example 5.
Figure 6:
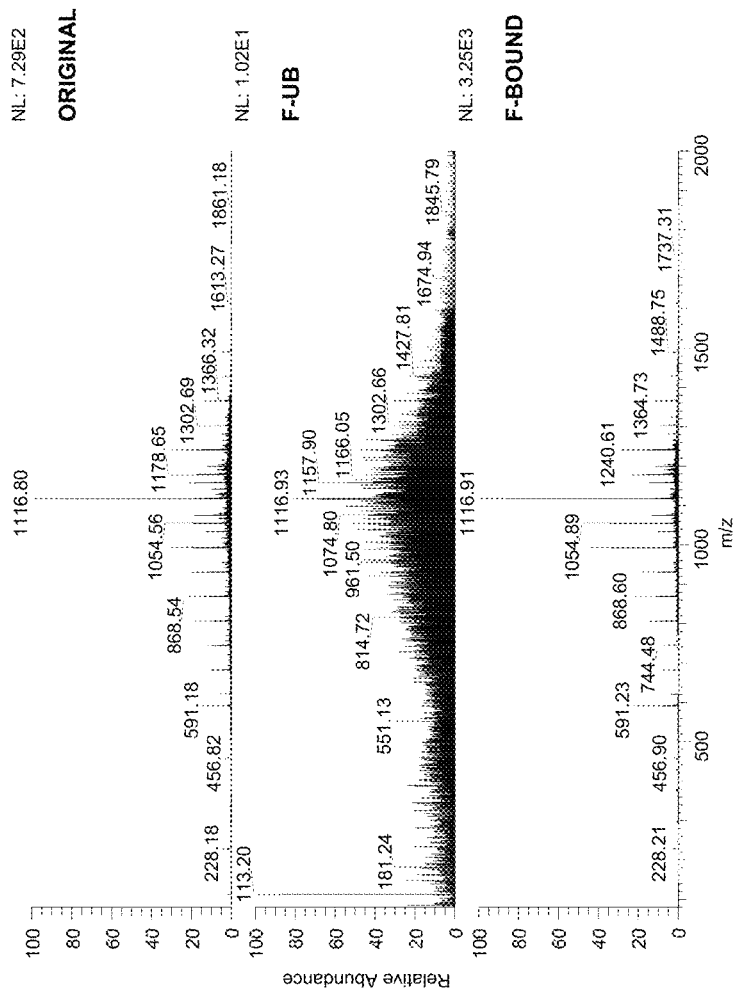
FIG. 6 shows the characteristic phlorotannin m/z species are enriched in the BOUND fraction in Example 5.

In the BOUND fraction, the set of peaks from 12-21 mins gave a set of m/z signals in negative mode that are characteristic of phlorotannins. They present as two series of m/z values that differ by 124 amu, which is the extension unit mass equivalent to phloroglucinol minus 2 H atoms, which have been noted previously in our research (Nwosu et al., 2010; Pantidos et al., 2014; Austin et al., 2018). The series from m/z 745, 869, 993, 1117, 1241, 1365 and 1489 could arise from successive phloroglucinol additions to a trimer with m/z value of 373 (e.g. triphlorethol) and signals at m/z 621, 745 etc could be pentaphloroethol, hexaphloroethol etc (Martinez et al., 2013). Therefore, the major peak at m/z 1117 could be a nonaphloroethol (see FIG. 5). It is notable that the tannin MS signals are approx. 4 fold enriched in the BOUND fraction (FIG. 6).

These series are apparent if MS spectra are averaged across the separation zone between 12 and 21 mins. Not all the phlorotannin components could be readily separated by elution on C18 columns and most elute as mixed peaks. There were also multiple isomers possible for each phlorotannin species. However certain peaks appeared to represent discrete phlorotannin components. In particular, the major peak at 17.4 mins yielded a discrete m/z signal at 1117, the peak at 16.82 yields m/z 1055, 17.62 yields m/z 1179 and the peak at 16.22 yields m/z 933. However, further work is required to define the structures of these components.

Figure 7:
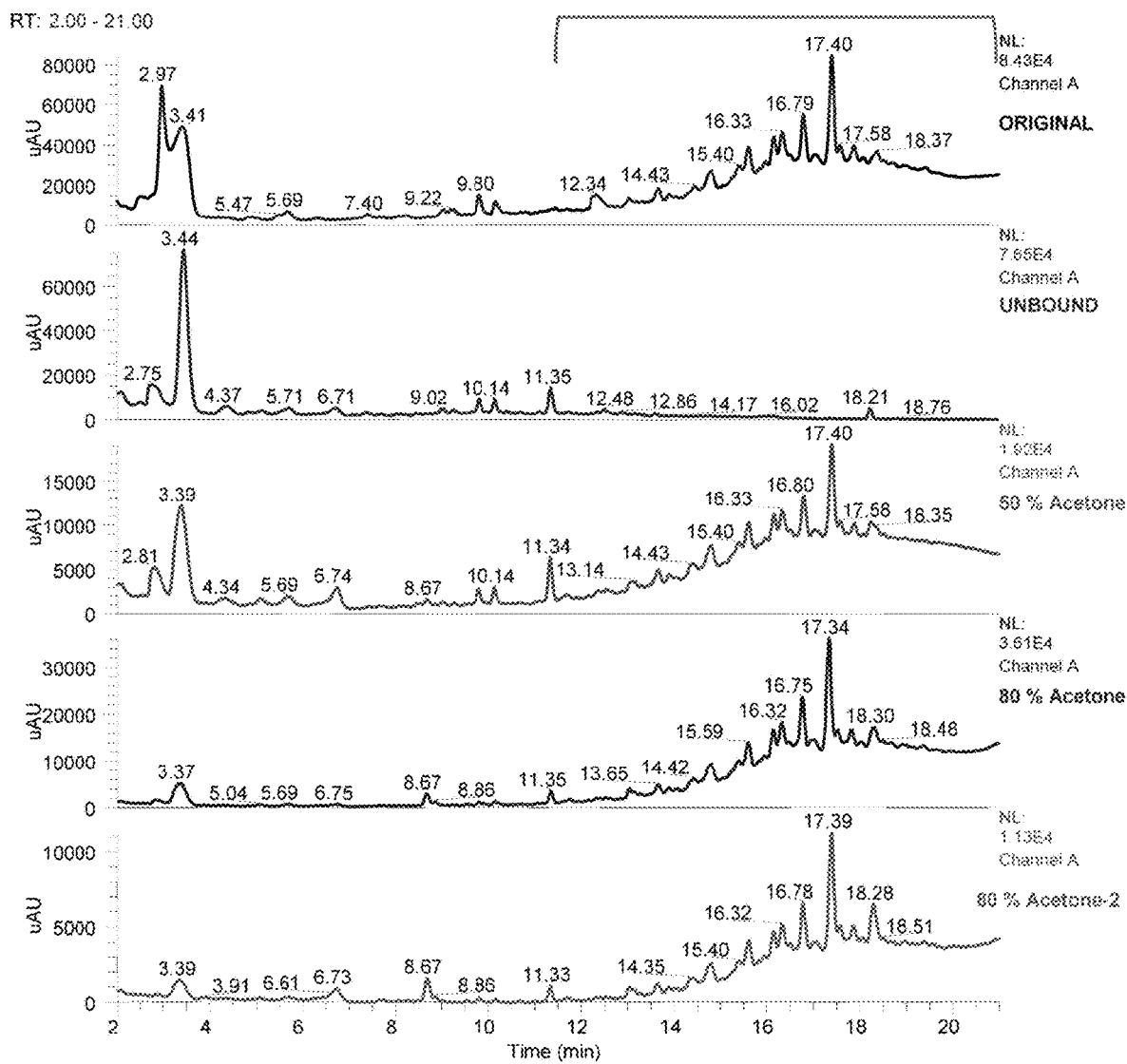
FIG. 7 shows Fractionation of phlorotannins on Sephadex LH20 in Example 5.
Figure 8:
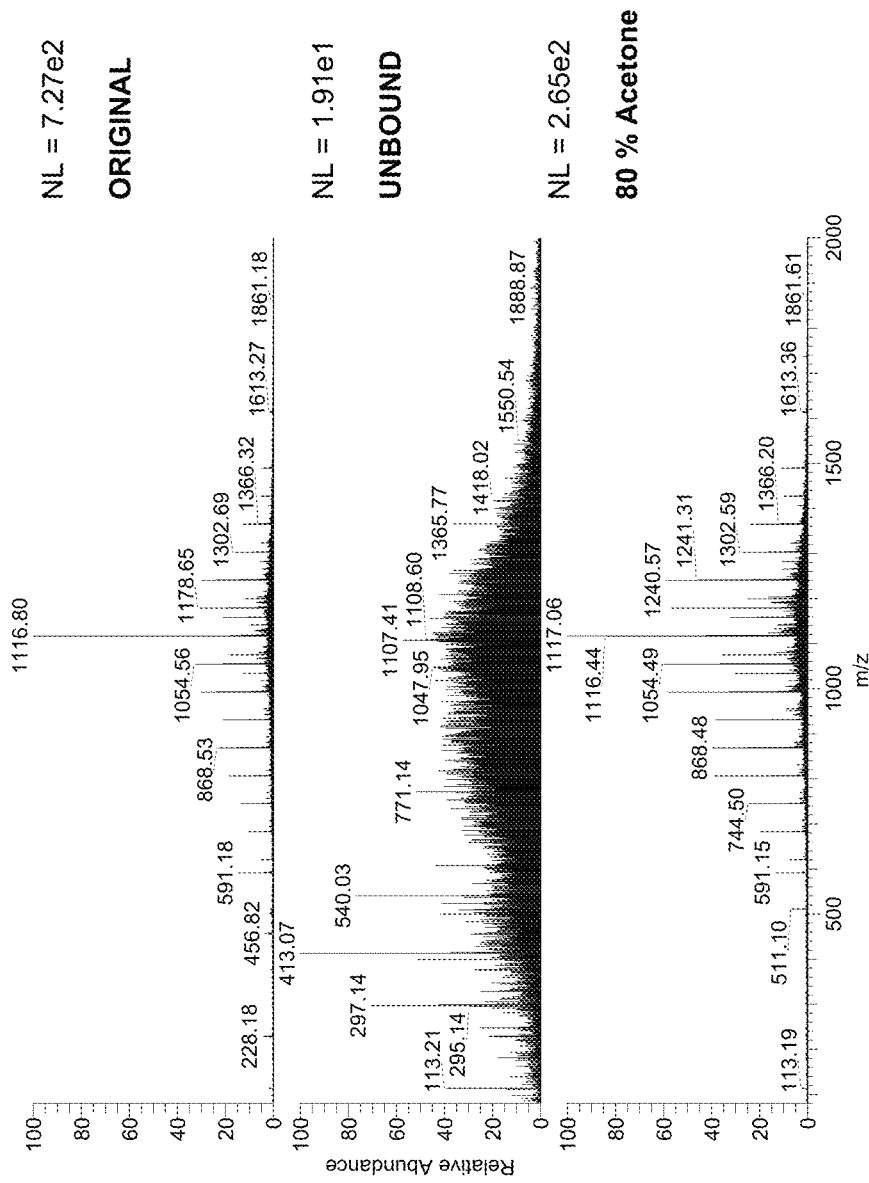
FIG. 8 shows the MS spectra of phlorotannin peaks in LH20 fractions in Example 5.

The late-eluting phlorotannin peaks were only present in the bound samples released from Sephadex LH20 by acetone. The fractionation could be improved by more stringent washing with 50% ethanol then moving directly to elution with 80% acetone but the results support the expected fractionation of phlorotannins by acetone (Pantidos et al., 2014), see FIG. 7.

Therefore, we can be confident that the BOUND fraction is enriched in phlorotannins of a similar kind as noted previously and with apparent masses in the DP 4-13 range, with a molecular mass of from about 1000 g/mol to about 3000 g/mol.

Further studies using Orbitrap MS provided further information.

Figure 9:
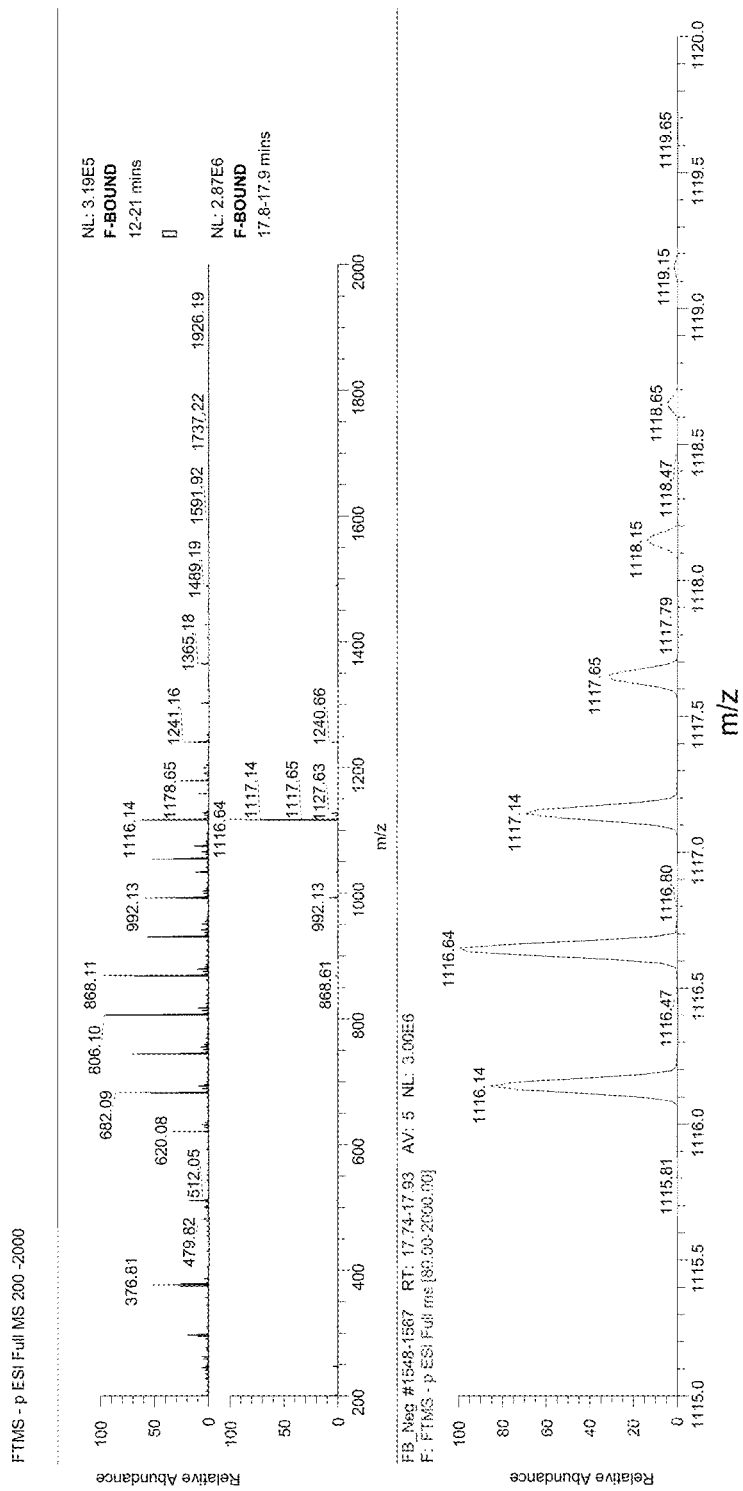
FIG. 9 shows the Orbitrap MS evidence for doubly charged phlorotannin components in Example 5.

On the Orbitrap, the F-BOUND sample showed the same late eluting UV peaks as before and gave similar MS spectra across the separation zone of 12-21 mins (FIG. 9).

As before, the major UV peak gave a MS signal at m/z 1117 but on closer examination this signal had 0.5 amu variants indicative of a $[M-H]^{2-}$ ion. As a doubly charged ion, the true mass would be twice as much and this suggests that this component was an oligomer of 18 phloroglucinol units rather than the nonaphloroethol described before. In fact all of the m/z values in the series from m/z 621 upwards were doubly charged which suggests that they are all larger than suggested by the original MS data. This range of DP fits with previous reports of phlorotannin structures from *Ascophyllum nodosum* (Steevensz et al., 2012).

LC-MS Evidence for Nature of Carbohydrate Components

Figure 10:
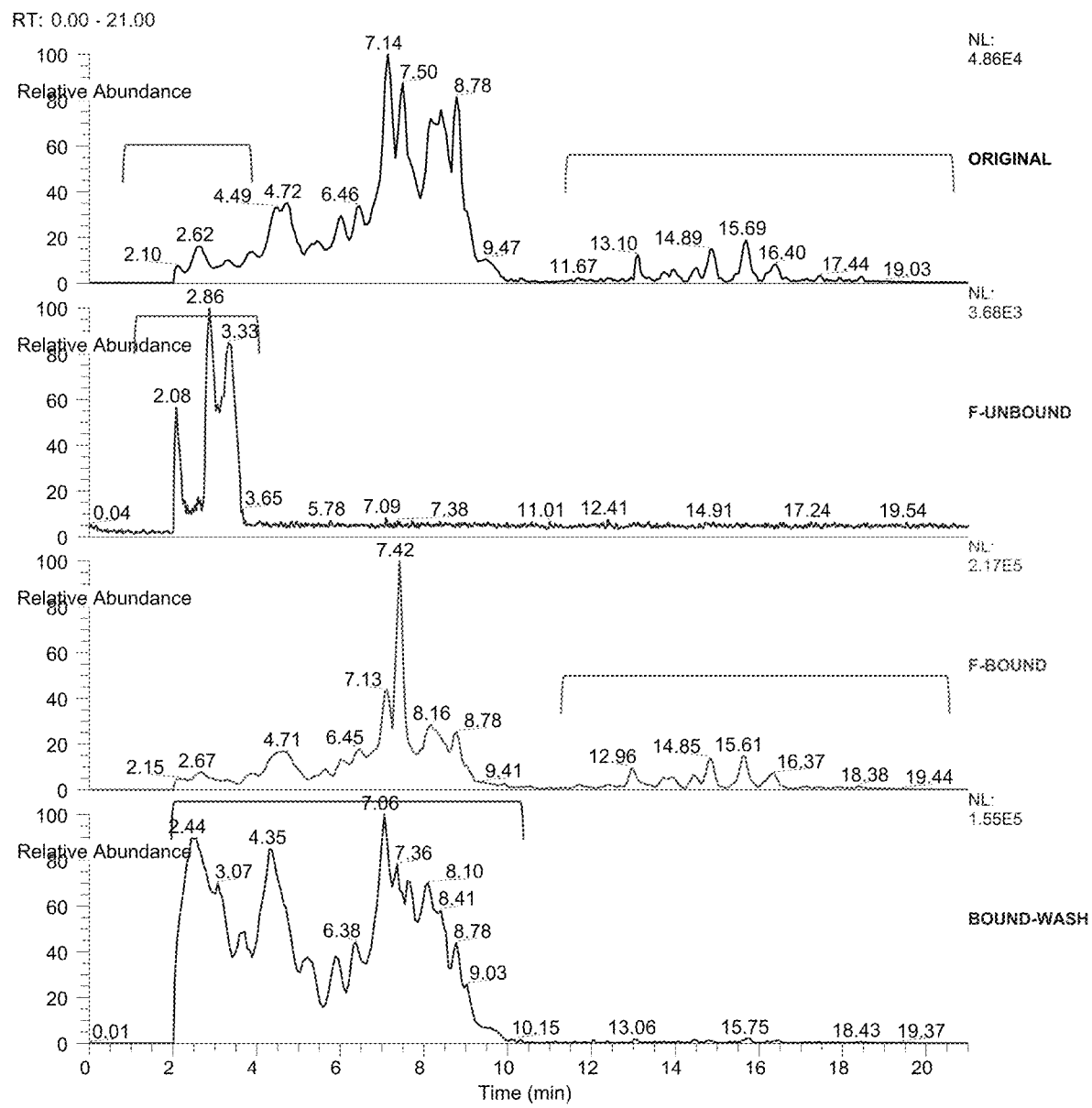
FIG. 10 shows the Positive mode LC-MS traces of original and SPE fractions in Example 5.

In positive mode, there are three sets of ionizing species in the Original sample (FIG. 10). There are the phlorotannin components from RT 12-21, earlier eluting components from RT 2-3.7 mins and another set of components that elute between 4-10 mins. The phlorotannins accumulate in the BOUND sample but the early eluting components are enriched in the UNBOUND whereas the other components are present in the BOUND fraction but enriched in the BOUND WASH fraction (see FIG. 10).

Figure 11:
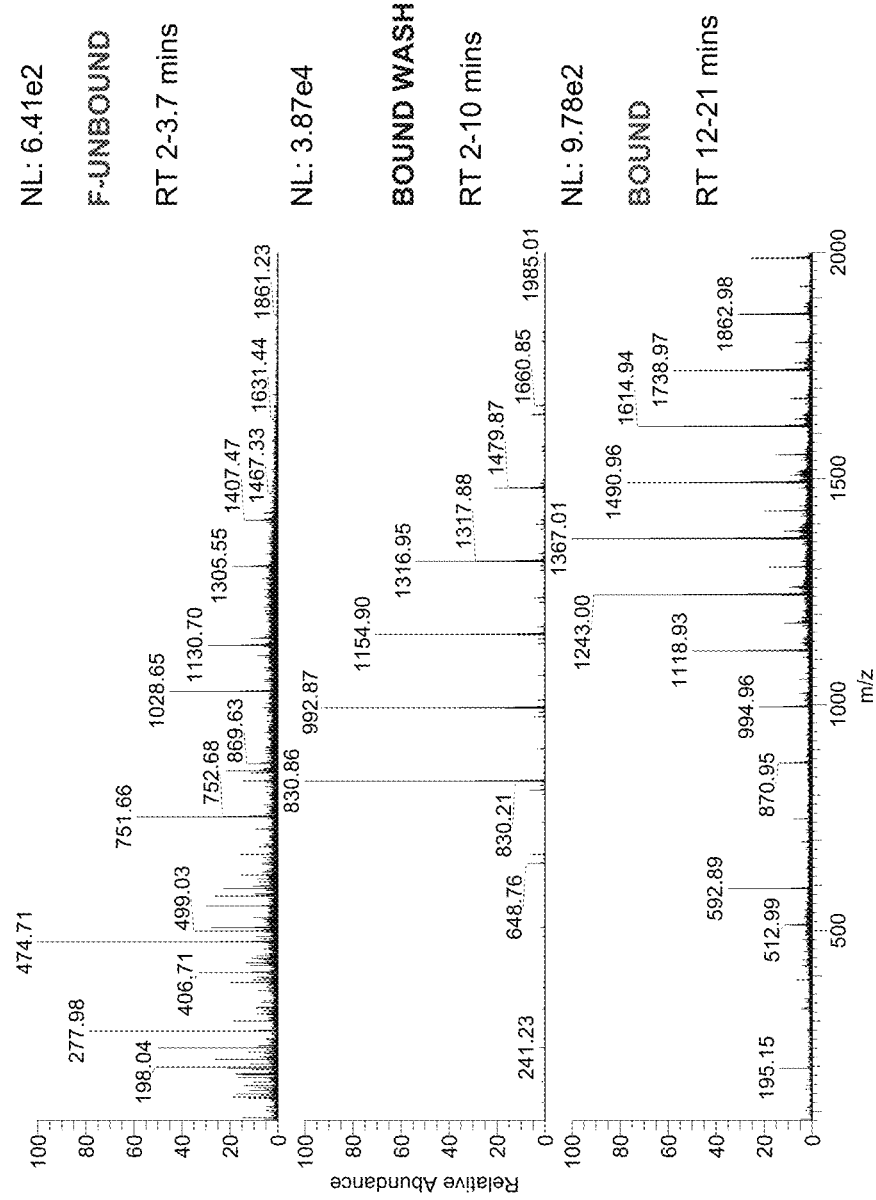
FIG. 11 shows the MS spectra of the 3 groups across their specific retention times in Example 5.

The phlorotannins give characteristic MS spectra (see trace 3, FIG. 11) and, as seen earlier, were enriched in the Bound fraction. The early eluting peaks also give specific MS signals (see trace 1, FIG. 11) but these are not similar to any reported seaweed components. Initial work suggests sulphated components may be present as these signals show neutral losses of 80 amu but identification of their nature will require further work.

The mid-eluting components, which are also enriched in the Bound Wash fraction, give an interesting series of MS signals (see trace 2, FIG. 9). Given that the Bound Wash fraction was enriched in CHOn compared to the original, it is possible that these components are carbohydrate in nature. There is a series starting at m/z $[M+H]^+=831$ that differ by 162 amu.

A similar pattern can also be seen in negative mode but positive mode gives more intense signals. Addition of 162 is characteristic of addition of hexose sugar groups (e.g. glucose) to an existing structure.

Figure 12:
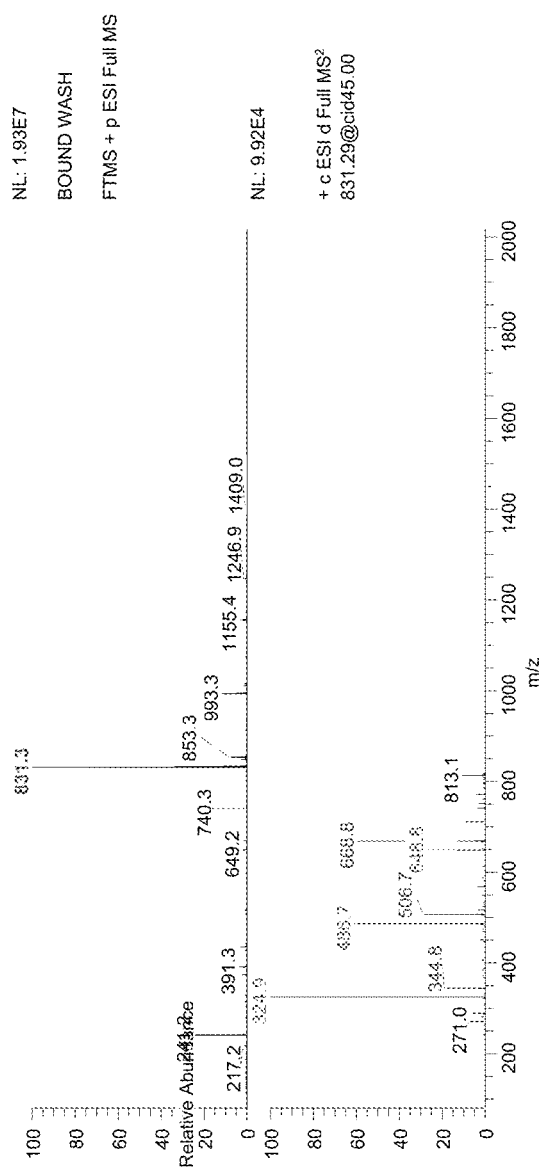
FIG. 12 shows the MS spectra of m/z 831 in the Bound Wash sample in Example 5.

The signal at m/z 831 fits with the molecular weight of laminaripentaitol (available from https://secure.megazyme.com/1~3-Beta-D-Laminaripentaitol) and signals at m/z 993, 1155, 1317 and 1479 could be due to the addition of hexoses to the core structure of this laminarin oligosaccharide with a terminal mannitol group. Mannitol terminated laminarins (M-laminarins) are known to occur in *Ascophyllum* (Kadam et al., 2014) and these m/z signals suggest that such oligosaccharides are present in the crude extract material. These m/z signals gave very poor fragmentation, so the runs were repeated on the Obritrap MS. The same series of signals were apparent in the Orbitrap MS data (FIG. 12).

The putative penta-oligosaccharide gave $MS^2$ fragments characterised by losses of 162 (loss of hexosyl group=glucose) or 182 (loss of mannitol). The signals at m/z 325 and 345 respectively could be protonated forms of a beta-linked glucose dimer (MW 324) and glucosyl-mannitol (MW 344). In addition, the m/z signal at 831 had an exact mass of 831.29499 which yielded a predicted formula of $C_{30}H_{55}O_{26}$ (error of <2 ppm) which fits with the formula for laminaripentaitol.

Similar MS spectra and fragmentation data and exact mass formulae could be obtained for other members of the series at m/z 669 (DP4), 933 (DP6) and 1155 (DP7).

In summary, the above results confirm that the crude extract is enriched with phlorotannins having a degree of polymerisation of from about 10 to about 30, corresponding to a molecular weight from about 1000 g/mol to about 3000 g/mol.

The above results also confirm that the crude extract can be purified into phlorotannin enriched and polysaccharide enriched fractions using Solid Phase Extraction SPE (Chromatographic method), with the phlorotannins present in the bound fraction.

Example 6—Separation of Crude (Hydroethanolic Extract) Using Tangential Flow Filtration TFF to Separate into Two Fractions (i) <1000 gmol−1; and (ii) >1000 gmol−1 a) Initial Handling/Observations

The extract was stored at 2-8° C., covered in foil, and the work was carried out protecting the samples from light as far as possible.

The solubility of the extract in water was investigated to inform subsequent mass balances. The extract was made up at 2% in water, thoroughly mixed, centrifuged, and the insoluble and soluble fractions were freeze-dried.

b) Tangential Flow Filtration (TFF) Experiments to Remove Low MW Material/Size-Based Separation An initial scoping run was conducted using an existing 1 kDa MW cut off hollow fibre cartridge on a Kros Flow Iii system (Spectrum), with subsequent runs carried out using a new cartridge with 2× surface area.

The extract samples were prepared by resuspension in water at 0.5%, followed by filtration down to GFC (1.2 um) (apart from first scoping experiment which was 0.4%).

The TFF concentration and diafiltration steps were standardised as far as possible between runs, with separation monitored by permeate conductivity.

All of the extract samples were freeze-dried and analysed by Folin-Ciocalteau assay and HPLC-size exclusion chromatography (SEC) with RI and PDA detectors.

Following the analysis and evaluation of samples, an additional fractionation run was also carried out on >1 kDa material using Vivaspin centrifugation units (Sartorius) at 30 kDa or 10 kDa MW cut off, to evaluate if further separation could be achieved using this approach.

An additional fractionation run was also carried out using a 5 kDa and 100 kDa MW cut off T-series membrane on a PALL centramate TFF system, to evaluate if this could improve separation. This has a larger surface area, allowing for higher loading of samples, although hold up volume is also larger.

c) Extraction Approaches Based on Solubility/Charge

All initial extraction experiments were carried out on >1 kDa material. Ethyl acetate was used to extract >1 kDa samples and generate an ethyl acetate soluble and insoluble fraction. Ethyl acetate was removed from samples by rotary evaporation and samples resuspended and freeze-dried. This was repeated on several batches of samples and the fractions were analysed by Folin-Ciocalteau assay and HPLC-SEC.

An alcohol extraction was carried out using 80% methanol on >1 kDa material. The 80% insoluble pellet was air-dried, resuspended and freeze-dried. Methanol was removed from the soluble fraction by rotary evaporation, and the resulting material freeze-dried. Fractions were analysed by Folin-Ciocalteau assay and HPLC-SEC.

Ion exchange chromatography was carried out on an ethyl acetate insoluble fraction to scope this method. The sample was loaded onto a Q-sepharose column in a Tris-NaCl buffer and eluted using a NaCl gradient. The two largest peaks were collected, dialysed and analysed.

d) Development of a Folin-Ciocalteau Assay to Estimate Polyphenol Content

A Folin-Ciocalteau assay was developed based on methods described in the literature and published theses. Phloroglucinol was used to generate a standard curve, and method optimised for timing and incubation temperatures. Results were generated in phloroglucinol equivalents. A PVPP blanking step was also introduced to allow estimation of how much of the signal can be attributed to phlorotannins, and how much may be other polyphenols or non-specific assay interference.

e) HPLC Size Exclusion Chromatography, HPLC C18 Analysis & GC-FID Monosaccharide Analysis GlycoMar's existing HPLC-SEC method was adapted to evaluate Byotrol sample fractions. A Shodex SB806M column calibrated with dextran standards (1-1400 kDa), with RI and PDA detection and aqueous mobile phase (Tris-HCl/NaCl) was used, with sample prepared in mobile phase.

Development of an HPLC method using a Kinetex XB C18 column (Phenomenex) has been explored to improve polyphenol evaluation. The mobile phase is 2% acetic acid 0-100% methanol gradient with samples prepared in methanol. Phloroglucinol was used as a control.

Monosaccharide analysis of selected samples was carried out using an in-house methanolysis and TMS derivatisation approach, followed by GC-FID analysis.

Sulphate analysis was carried out using an in-house modified Terho method based on barium chloride.

Results Overview a) Initial Observations

Dry weight yields indicated only a minimal amount of the original sample (~0.4% w/w) was water insoluble debris, such as cellular material.

b) Tangential Flow Filtration Experiments to Remove Low MW Material.

TABLE 3

Scoping run using existing 1 kDa MW cut off hollow fibre unit, 2 g sample loading:

| TFF run | Fraction | Yield % (w/w) | Folin PG[1] equivalents μg/ml |
|---|---|---|---|
| 23 Apr. 2018* | >1 kDa | 9.4 | 60.4 |
|  | <1 kDa | 57.8 | 2.6 |

*diafiltration permeate yield not quantified for this run
[1]phloroglucinol equivalents There was lower than expected recovery of >1 kDa material from this unit (based on previous CEVA data) and evidence of polyphenols sticking to the fibres. All subsequent 1 kDa runs were carried out using a new hollow fibre unit with higher surface area (Table 4 below).

TABLE 4

Subsequent runs using a new 1 kDa MW cut off hollow fibre unit with 2X surface area, 5 g sample loading:

| TFF Run | Fraction | Yield % (w/w) | Folin PG equivalents μg/ml |
|---|---|---|---|
| 7 May 2018 | >1 kda | 38.5 | 20.0 |
|  | <1 kDa | 46.5 | 2.6 |
| 15 May 2018* | >1 kda | 31.4 | 21.8 |
|  | <1 kda | 42.5 | 2.6 |
| 28 May 2018 | >1 kda | 21.1 | 34.9 |
|  | <1 kda | 43.2 | 2.6 |

*> and < 1 kDa fractions from this run sent to Byotrol. (Additional run from 12 Jun. 2018 still to be analysed)

The >1 kDa fraction % yield on the new unit was much higher than the scoping run, under the same handling conditions (volumes, concentration and diafiltration). Coloured fouling of the unit was again observed, but performance checks indicated it recovered well after use. However, >1 kDa yield reduced over time, probably suggesting a stabilisation of the unit.

Folin assay data: All the TFF fractions were tested in the Folin-Ciocalteau assay and the results suggested that polyphenol was retained in the >1 kDa fraction (see Table 1 & 2 above). If any polyphenol was present in the <1 kDa fraction it was below the limit of quantification of the Folin assay. Samples were also very different by appearance, with the >1 kDa fraction being dark brown and flakey, and the <1 kDa fraction being cream/white, crumbly and slightly tacky.

Figure 13:
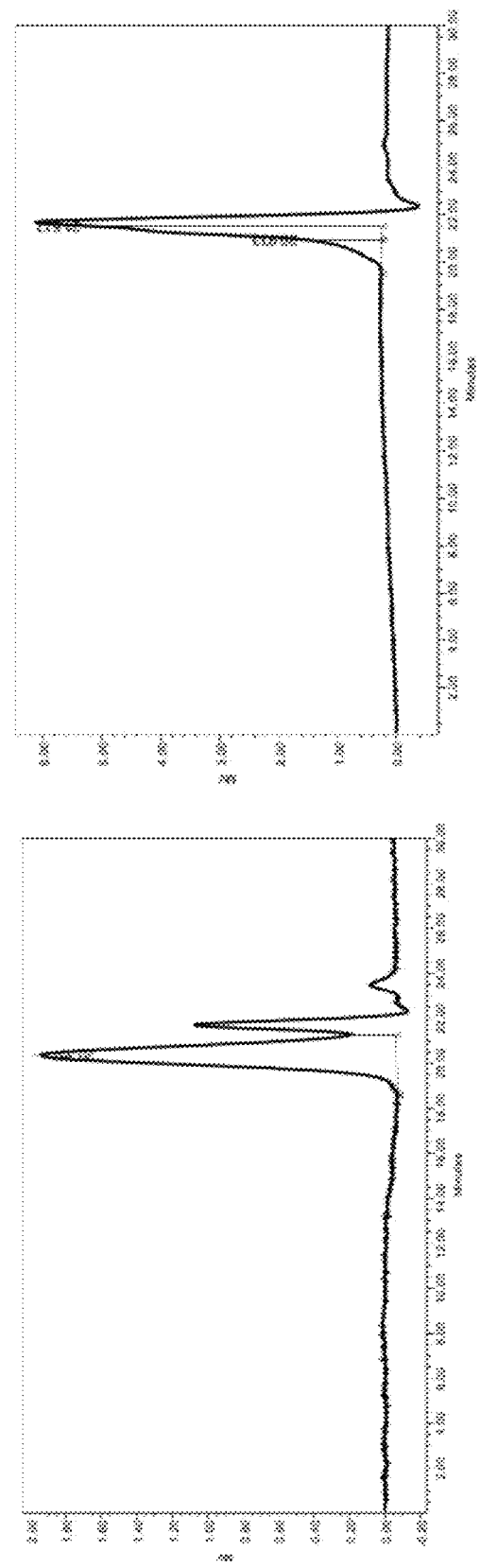
FIG. 13 shows the HPLC-SEC RI detection of >1 kDa (left) and <1 kDa (right) TFF fractions of the extract of the invention in Example 6.

HPLC analysis: Preliminary HPLC-SEC analysis confirmed the low MW profile of both fractions, but with clear differences between the >1 and <1 kDa fractions (FIG. 13 below: >1 kDa left, <1 kDa right). The current method is not optimised to resolve this low MW material, but it is clear from the chromatography that the <1 kDa fraction is comprised of lower MW aqueous soluble material (ie later retention times) than the >1 kDa fraction. This is potentially due to the large amount of mannitol present in the <1 kDa fraction (mannitol standard elutes at Rt of 21.3 mins). The RI chromatography profile of these samples was consistent across all the TFF batches.

A dialysis trial was also carried out to assess yield using other separation methods (Table 5 below).

TABLE 5

Dialysis trial:

| 1 kDa MWCO | Sample/g | >1 yield % (w/w) starting | Folin PG equivalents μg/ml |
|---|---|---|---|
| Dialysis 7 May 18 | 0.5 | 12.6 | 44.5 |

Conclusions from fractionation using 1 kDa MW cut off TFF were that it successfully separated <1 kDa material from the sample. >1 kDa material may contain varying amounts of smaller components, dependent on success of the TFF step. Polyphenols were retained in the >1 kDa fraction. Fouling of the membrane with polyphenol like material was a problem.

c) Extraction Approaches Based on Solubility & Charge.

Attempts to further sub-fractionate >1 kDa fractions were carried out by extraction in either ethyl acetate or 80% methanol.

TABLE 6

Solubility based fractionation of >1 kDa fractions of 17/11/21 ASCOX

| TFF Run Date | Fraction | Yield % (w/w) of >1 kDa fraction | Folin PG equivalents μg/ml |
|---|---|---|---|
| 23 Apr. 2018 | EtAc soluble | 47.8 | 52* |
| 2018 | EtAc insoluble | 56.4 | 53.4* |
| 7 May 2018 | EtAc soluble | 2.6 | 21 |
| 2018 | EtAc insoluble | 86.8 | 22 |

| | | Yield % (w/w) of EtAc soluble fraction | |
|---|---|---|---|
| 7 May 2018 (200 mg) | 80% MeOH soluble | 87.1 | 21.5 |
| | 80% MeOH insoluble | 1.7 | 12 |

*prior of final Folin assay method development.

A repeat extraction with 80% MeOH and higher loading is still to be analysed

Ethyl acetate extraction: A small amount of >1 kDa material was soluble in ethyl acetate, but yield was low, and the extraction appeared to be non-specific. In later batches much of the material remained in the insoluble fraction with polyphenol being detected in both soluble and insoluble fractions (Table 6 above). In the second trial only a small % of the >1 kDa fraction was soluble in the ethyl acetate. These samples also had very similar chromatography and MW profile as far as could be distinguished by the HPLC-SEC analysis.

80% methanol extraction: Due to lack of success with ethyl acetate approach, a Sephadex LH 20 approach was considered. However, due to problems with polyphenols sticking on resins and on the membrane filters, it was decided this approach was unlikely to result in an improved separation. Therefore, differential solubility in 80% methanol was tested instead of ethyl acetate. Literature suggests that polyphenols are most soluble in 80% methanol (rather than 100% methanol) with a lower % methanol resulting in solubilisation of carbohydrates as well, ie. carbohydrates should be insoluble in 80% methanol, allowing separation of these species.

Figure 14:
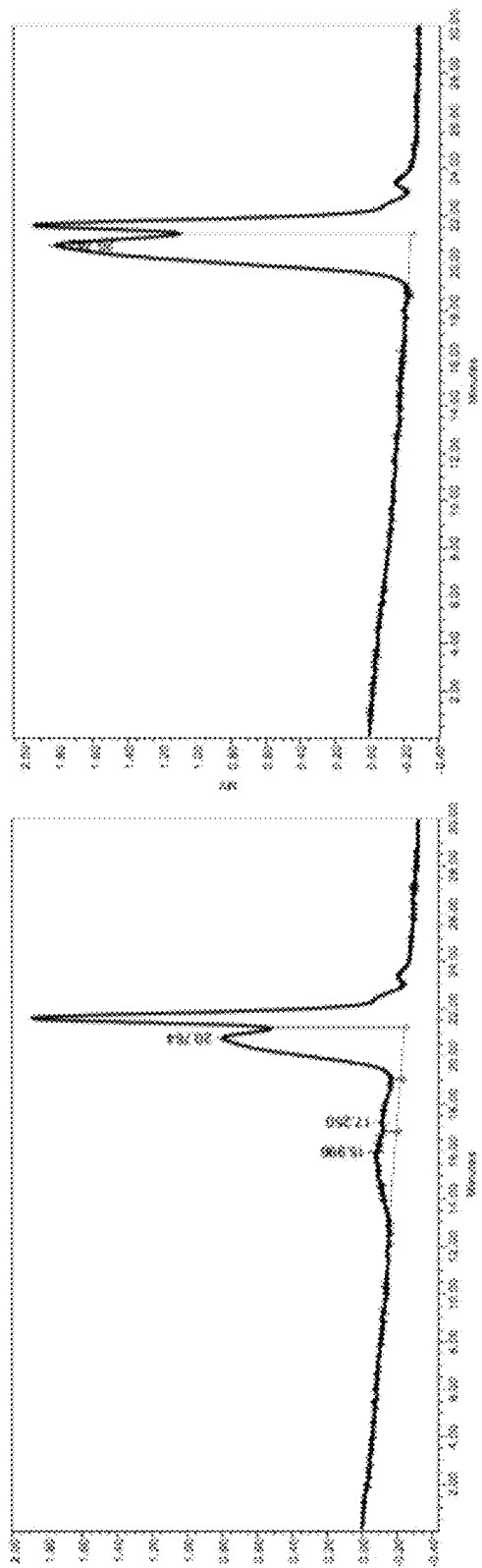
FIG. 14 shows the Left: HPLC-SEC RI detection of 80% MeOH insoluble fraction (higher MW material [ie earlier retention times] was observed). Right: HPLC-SEC RI detection of 80% soluble TFF fraction Example 6.

87.1% of a >1 kDa fraction was soluble in 80% methanol (Table 6 above). There was only a low yield of the methanol insoluble material (~1-2%), although this appeared to have a reduced polyphenol content (Table 6 above). Preliminary HPLC-SEC of these fractions indicated that the insoluble material comprised higher MW components, which did not appear to be polyphenol (by MW, and absorbance spectra) (FIG. 14, left). The 80% soluble material comprised all low MW material (FIG. 14, right). Analysis of monosaccharide and sulphate content of these samples suggested that fucoidan was present in the 80% insoluble component, but it was mixed with other compounds, including some polyphenols (Table 7 below). Glucose was also detected in the 80% MeOH soluble fraction and the origin of this sugar was not clear. Laminarin is unlikely to be soluble in 80% MeOH, although this should be further evaluated.

TABLE 5

Monosaccharide analysis and sulphate data for 80% methanol extraction fractions. 80% MeOH insoluble material contains fucose and galactose, indicative of fucoidan. Sulphate is present, but at lower amounts than would be expected for pure fucoidan. Glucose is also present in both soluble and insoluble fractions.

| Monosaccharide | 80% MeOH insoluble | 80% MeOH soluble |
|---|---|---|
| Arabinose | 6.21% | 5.70% |
| Rhamnose | 2.23% | 0.82% |
| Fucose | 11.73% | 0.00% |
| Xylose | 4.71% | 0.00% |
| GalA | 0.00% | 0.00% |
| Mannose | 1.54% | 0.00% |
| Galactose | 4.37% | 1.22% |
| Glucose | 65.19% | 89.13% |
| Glucuronic acid | 4.02% | 3.12% |
| N-acetyl galactosamine | 0.00% | 0.00% |
| N-acetyl glucosamine | 0.00% | 0.00% |
| Recovery % | 20.60% | 33.70% |
| % sulphate | 4.2 | LOD |

Conclusions from solubility based fraction approaches were that ethyl acetate was not effective in partitioning components in the >1 kDa fractions. Whilst the fractions from the 80% methanol extraction were different in composition, the yield of the insoluble fraction was only 1% of starting material (w/w), suggesting that if this is fucoidan rich, then it is only present at very low levels. Glucose was also detected in the 80% MeOH soluble fraction and the origin of this sugar is not clear. Laminarin is unlikely to be soluble in 80% MeOH, although this should be further evaluated. Further monosaccharide analysis is being carried out on other samples, incorporating a mannitol and laminarin control.

Ion exchange chromatography: Despite the lack of fractionation using ethyl acetate, ion exchange chromatography of an ethyl acetate insoluble fraction was carried out to evaluate this approach. Sodium chloride gradient elution resulted in multiple small peaks over the whole gradient, with evidence of polyphenols stuck to the top of the column. There was minimal baseline resolution and due to the material stuck on the column, it was not clear how much of the sample was being resolved. However, the two largest peaks were collected, dialysed and freeze-dried. Analysis of these peaks suggested they did not contain polyphenols (Table 8 below), although the low recovery may skew quantification. Preliminary HPLCSEC also suggested some higher MW components were present, but monosaccharide analysis suggested only minimal carbohydrate was present (recovery in this analysis was <5%). It may be possible to separate other components from polyphenols using this approach, but due to the polyphenols sticking to the column, and multiple peaks eluting, the method is very difficult to control and scale up.

TABLE 8

Ion exchange chromatography of an EtAc insoluble, >1 kDa TFF fraction of 17/11/21 ASCOX

| TFF Run | Fraction | Yield % (w/w) | Folin PG equivalents μg/ml |
|---|---|---|---|
| 23 Apr. 2018 >1 kDa fraction | EtAc soluble | 47.8 | 52* |
| | EtAc insoluble | 56.4 | 53.4* |
| 23 Apr. 18 EtAc insoluble (70 mg) | QSepharose peak 28-44 mins | 6.9 | 1.4 |
| | QSepharose peak 58-72 mins | 14.3 | 1.2 |

*prior to final Folin assay method development d) Additional Fractionation Approaches to Target Carbohydrate and Polyphenol Components.

Attempts to fractionate >1 kDa samples to yield fractions enriched for polyphenol or carbohydrate had been largely unsuccessful based on solubility (EtAc/80% MeOH), and handling (such as ion-exchange) was limited by the nature of polyphenols and their non-specific adhesion to resins.

Whilst preliminary in nature, all the HPLC data indicated that polyphenols are low MW (largely <5 kDa, with literature indicating maybe <1 kDa). Therefore, based on the predicted low MW of polyphenols, further trials were carried out using MW cut off separations, to attempt to further fractionate the sample.

Vivaspin centrifugal separators: Further fractionation by MW using Vivaspin centrifugal units was carried out using two different MW cut offs with two 300 mg samples of >1 kDa 17/11/21 ASCOX. Whilst the resulting fractions were different in appearance (FIG. 4 below), polyphenol was detected by Folin assay in all fractions other than the <10 kDa fraction (Table 7 below). These and other samples confirm that the colour of samples does appear to correlate with the amount of polyphenol present.

TABLE 9

Vivaspin separation of >1 kDa material of 17/11/21 ASCOX

| Vivaspin MWCO/kPa | Yield % starting w/w | Description | Folin PG equivalents µg/ml |
|---|---|---|---|
| >10 | 45.2 | Coloured | 46.4 |
| <10 | 51.8 | Clear | 2.6 |
| >30 | 35 | Coloured | 43.9 |
| <30 | 57.5 | Slightly coloured | 11 |

TFF using higher MW cut off membranes: Due to the difficulty in separating polyphenols from other components in 17/11/21 ASCOX, a trial was also carried out using a PALL centramate TFF system and 100 and 5 kDa T-series membranes. This system would also allow for a much high loading of sample (20 g), in order to generate larger amounts of fractions. 17/11/21 ASCOX was solubilised and filtered, as described above, prior to processing on the TFF. Membranes were used sequentially ie. sample passed through the 100 kDa and then all permeate (including from the diafiltration step) being pooled and applied to the 5 kDa membrane. See Table 10 for yield data.

TABLE 8

Higher MW cut off trial using centramate 100 and 5 kDa T-series membranes

| Sample/g | >100 kDa yield % (w/w) starting | 5-100 kDa yield % (w/w) starting | <5 kDa yield % (w/w) starting* |
|---|---|---|---|
| 4 Jun. 2018 | 20 g | 1.4 | 9.8 | 44.4 |

*Dialfiltration permeate yield not included

Preliminary HPLC-SEC analysis suggested that higher MW material from 17/11/21 ASCOX is enriched in the >100 kDa fraction. A defined peak is present in the 5-100 kDa fraction, with most low MW material present in the <5 kDa fraction. This approach, with a molecular sieve much higher than polyphenol MW, along with the <30 kDa vivaspin samples, suggested polyphenols will pass through filtration membranes if the MW cut off is much larger than the predicted polyphenol MW. However, some polyphenol is still retained, probably due to a membrane interaction or formation of large aggregates. It may be possible to improve this separation by changing conditions on the membrane—eg. less ionic, or non-polar conditions, low % alcohol, to prevent aggregation, and get a more accurate size-based separation of polyphenols.

Conclusions from additional centrifugal filtration and TFF approaches are that size-based membrane fractionation is limited due to membrane interaction by polyphenols. However, the use of a higher MW cut off allows for improved separation, with prediction of fucoidan being retained in the >100 kDa fraction, and the majority of polyphenols passing through the membrane.

Example 7—Anti-Viral Activity of the Crude Extract and the Fractions Obtained in Examples 5 and 6 Above The hydrophilic, hydrophobic, (i)<1000 gmol$^{-1}$; and (ii) >1000 gmol$^{-1}$ fractions obtained in Examples 5 and 6 respectively, were then subjected to anti-viral testing against Murine norovirus using a method as described in Example 4.

Figure 15:
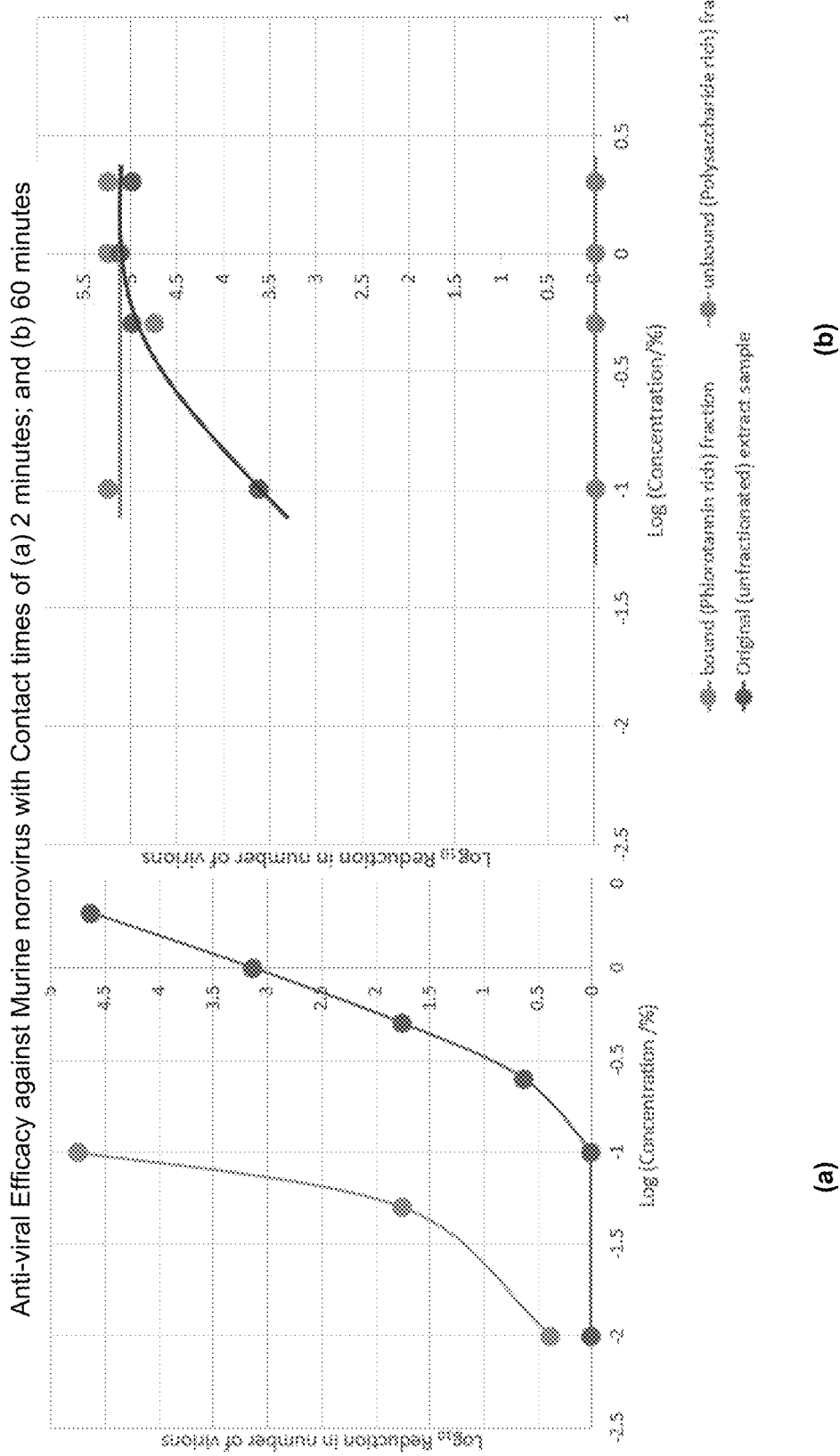
FIG. 15 shows the anti-viral activity of the Bound and Unbound fractions in Example 7.
Figure 16:
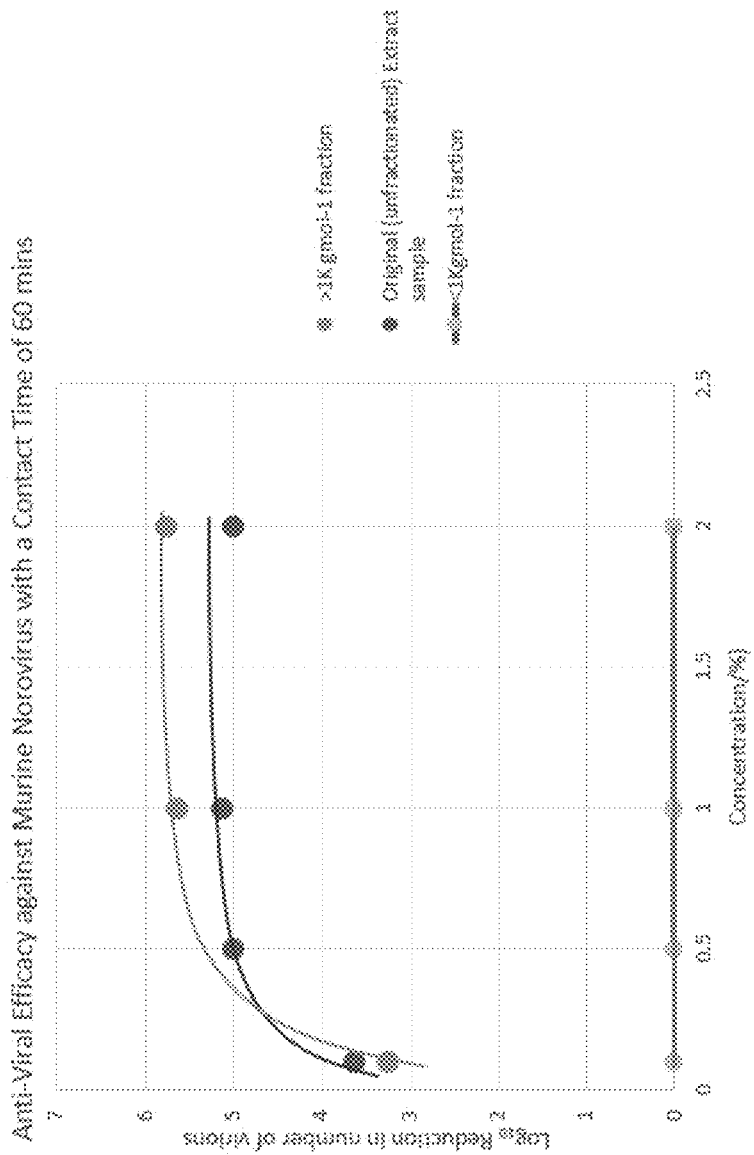
FIG. 16 shows the anti-viral activity of the <1000 gmol−1; and (ii) >1000 gmol−1 fractions Example 7.

The results are shown in FIGS. 15 and 16 and confirm that it is the BOUND (hydrophobic) and >1000 gmol−1 fraction that are active.

Example 8—Comparison of the Anti-Viral Activity of Seaweed Extract and Phlorotannin Enriched Fraction with Epigallocatechin, a Polyphenol Extracted from Green Tea Seaweed extracts obtained from Example 3 (crude extract) and Example 5 (bound extract) were used, together with Epigallocatechin gallate (≥95%) obtained from Sigma Aldrich. The test conditions used were as described in Example 7.

Figure 17:
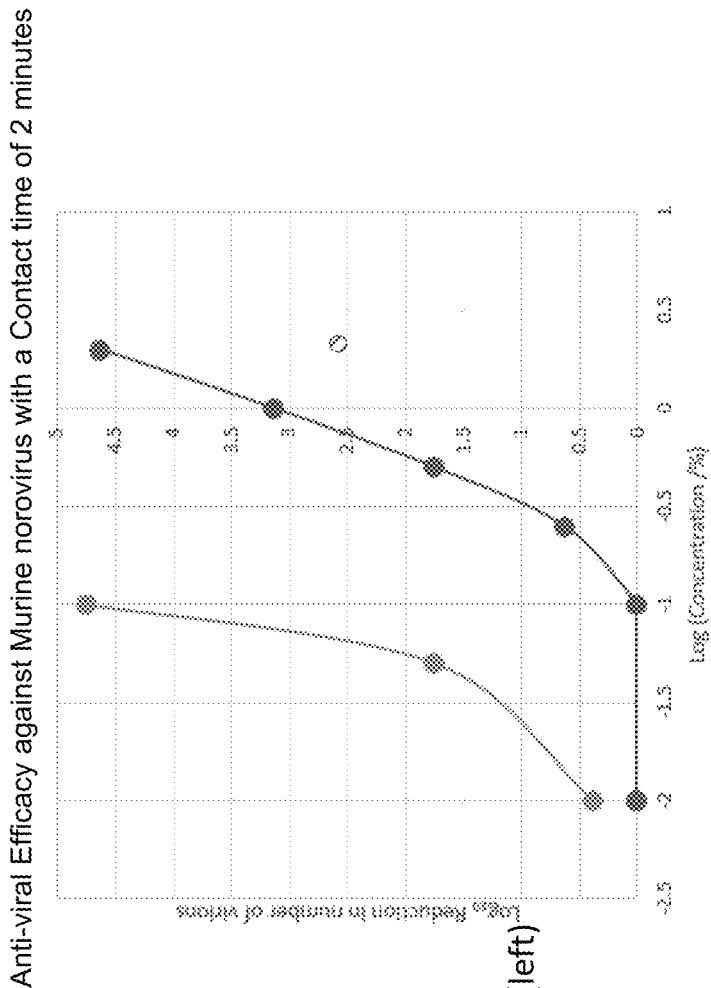
FIG. 17 shows a comparison of the anti-viral activity of seaweed extract and phlorotannin enriched fraction with Epigallocatechin, a polyphenol extracted from Green Tea in Example 8.
Figure 17:
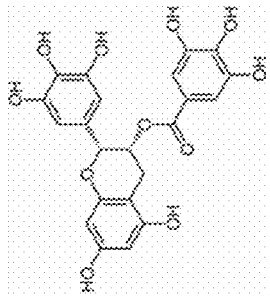

The results show that the anti-viral activity for both the crude and bound extracts display significant anti-viral activity (see FIG. 17).

The invention claimed is:

1. An extract of Ascophyllum nodosum, wherein the extract comprises from 60% to 95% by weight based on the dry weight of the extract of one or more phlorotannins and wherein at least 70% by weight of the one or more phlorotannins based on the dry weight of the phlorotannins in the dry extract has a molecular mass of from about 1000 g/mol to about 3000 g/mol.

2. The extract according to claim 1, wherein the extract comprises phloroglucinol units are linked via ether linkages, phenol linkages, dibenzodioxin linkages, or a mixture thereof.

3. The extract according to claim 1, wherein the extract comprises phloroglucinol units are linked in linear and/or branched chains.

4. A method of obtaining an extract according to claim 1, comprising contacting Ascophyllum nodosum with a hydroalcoholic extraction solvent.

5. The method according to claim 4, wherein the hydroalcoholic extraction solvent is 60:40 ethanol: water.

6. The method according to claim 4, further comprising extraction with an organic solvent.

7. The method according to claim 4, further comprising purifying the extract.

8. An anti-viral composition comprising the extract according to claim 1.

9. The anti-viral composition according to claim 8, wherein the composition comprises the one or more phlorotannins in an amount of from 0.0025 to 50% by weight of the composition.

10. A method of treating or preventing a viral infection, comprising administering the extract according to claim 1 to a subject in need thereof.

11. A method of treating or preventing a viral infection, comprising administering the composition according to claim 8 to a subject in need thereof.

12. A method of reducing or controlling a virus on or at a surface, comprising applying the extract according to claim 1 to the surface.

13. A method of reducing or controlling a virus on or at a surface, comprising applying the composition according to claim 8 to the surface.

14. The method of claim 10, wherein the virus is enveloped or non-enveloped.

15. The method of claim 12, wherein the virus is enveloped or non-enveloped.

16. The method of claim 10, wherein the virus is selected from one or more of group I, II, III, or V of the Baltimore classification of viruses.

17. The method of claim 12, wherein the virus is selected from one or more of group I, II, III, or V of the Baltimore classification of viruses.

* * * * *